US 6,923,907 B2

(12) United States Patent
Hobbs et al.

(10) Patent No.: US 6,923,907 B2
(45) Date of Patent: *Aug. 2, 2005

(54) SEPARATION COLUMN DEVICES AND FABRICATION METHODS

(75) Inventors: Steven E. Hobbs, West hills, CA (US); Matthew M. Gregori, Los Angeles, CA (US); Christoph D. Karp, Pasadena, CA (US); Jeffrey A. Koehler, Pasadena, CA (US); Paren P. Patel, Sierra Madre, CA (US); Joseph F. Covington, San Gabriel, CA (US)

(73) Assignee: Nanostream, Inc., Pasadena, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 10/366,985

(22) Filed: Feb. 13, 2003

(65) Prior Publication Data

US 2003/0150806 A1 Aug. 14, 2003

Related U.S. Application Data

(60) Provisional application No. 60/357,683, filed on Feb. 13, 2002, and provisional application No. 60/415,896, filed on Oct. 3, 2002.

(51) Int. Cl.[7] ............................................... B01D 15/08
(52) U.S. Cl. ..................... 210/198.2; 210/656; 422/70; 422/100; 73/61.52
(58) Field of Search .............................. 210/656, 198.2; 422/70, 100; 96/101; 73/61.52

(56) References Cited

U.S. PATENT DOCUMENTS

| | | | |
|---|---|---|---|
| 3,449,938 A | 6/1969 | Giddings | 73/23 |
| 4,301,139 A | 11/1981 | Feingers et al. | 424/1 |
| 4,424,127 A | 1/1984 | Roeraade | 210/198.2 |
| 4,496,461 A | 1/1985 | Leeke et al. | 210/198.2 |

(Continued)

FOREIGN PATENT DOCUMENTS

| | | | |
|---|---|---|---|
| EP | 1 106 244 A2 | 6/2001 | ............ B01J/19/00 |
| EP | 1178309 A1 | 2/2002 | |
| WO | WO 97/30347 | 8/1997 | |
| WO | WO 98/04909 | 2/1998 | .......... G01N/27/26 |
| WO | WO 99/19717 | 4/1999 | .......... G01N/25/22 |
| WO | WO 99/29497 | 6/1999 | ............ B32B/3/00 |
| WO | WO 99/33559 | 7/1999 | ............ B01J/19/00 |
| WO | WO 99/34909 | 7/1999 | ............ B01J/19/00 |
| WO | WO 99/48599 | 9/1999 | ............. B01F/5/06 |
| WO | WO 99/60397 | 11/1999 | ......... G01N/33/483 |
| WO | WO 00/21659 | 4/2000 | ............ B01J/19/00 |
| WO | WO 00/31528 | 6/2000 | |
| WO | WO 00/51720 A3 | 9/2000 | |
| WO | WO 01/09598 A1 | 2/2001 | |
| WO | WO 01/38865 A1 | 5/2001 | |
| WO | WO 01/38865 | 5/2001 | ......... G01N/27/447 |
| WO | WO 01/50123 A1 | 7/2001 | |
| WO | WO 01/86283 A3 | 11/2001 | |
| WO | WO 02/22250 A2 | 3/2002 | |
| WO | WO 02/28509 | 4/2002 | ........... B01D/53/00 |
| WO | WO 02/28532 A | 4/2002 | |
| WO | WO 02/28532 | 4/2002 | ............ B01L/3/00 |
| WO | WO 02/056006 A2 | 7/2002 | |

OTHER PUBLICATIONS

Ericson, Christer et al., *Electroosmosis–and Pressure Driven Chromatography in Chips Using Continuous Beds*, "Analytical Chemistry," vol. 72, No. 1, Jan. 1, 2000, pp. 81–87.

(Continued)

*Primary Examiner*—Ernest G. Therkorn
(74) *Attorney, Agent, or Firm*—Vincent K. Gustafson

(57) ABSTRACT

Pressure-driven microfluidic separation devices, such as may be used for performing high performance liquid chromatography, are provided. Multiple separation columns may be defined in a single device and packed with stationary phase material retained by porous frits. One or more splitters may be provided to distribute slurry and/or mobile phase among multiple separation columns. In one embodiment, separation devices are substantially planar and fabricated with multiple device layers. Systems and methods employing slurry for packing separation devices are also provided.

57 Claims, 19 Drawing Sheets

U.S. PATENT DOCUMENTS

| | | | |
|---|---|---|---|
| 4,505,539 A | 3/1985 | Auracher et al. | 350/96.15 |
| 4,604,198 A | 8/1986 | Dailey et al. | 210/198.2 |
| 4,868,129 A | 9/1989 | Gibbons et al. | 436/179 |
| 4,891,120 A | 1/1990 | Sethi et al. | 204/299 R |
| 4,990,259 A * | 2/1991 | Kearney et al. | 210/659 |
| 5,135,627 A | 8/1992 | Soane | 204/182.8 |
| 5,190,658 A | 3/1993 | Vilenchik et al. | 210/656 |
| 5,194,133 A | 3/1993 | Clark et al. | 204/299 |
| 5,376,252 A | 12/1994 | Ekström et al. | 204/299 |
| 5,478,751 A | 12/1995 | Oosta et al. | 436/165 |
| 5,658,413 A | 8/1997 | Kaltenbach et al. | 156/272.8 |
| 5,792,943 A | 8/1998 | Craig | 73/61.52 |
| 5,872,010 A | 2/1999 | Karger et al. | 436/173 |
| 6,004,450 A | 12/1999 | Northrup et al. | 205/656 |
| 6,066,848 A | 5/2000 | Kassel et al. | 250/288 |
| 6,074,725 A | 6/2000 | Kennedy | 428/188 |
| 6,090,278 A | 7/2000 | Lally et al. | 210/198.2 |
| 6,103,199 A | 8/2000 | Bjornson et al. | 422/100 |
| 6,129,973 A | 10/2000 | Martin et al. | 428/166 |
| 6,149,815 A | 11/2000 | Sauter | 210/635 |
| 6,171,486 B1 | 1/2001 | Green et al. | 210/198.2 |
| 6,197,198 B1 | 3/2001 | Messinger et al. | 210/656 |
| 6,210,986 B1 | 4/2001 | Arnold et al. | 438/42 |
| 6,221,252 B1 | 4/2001 | Hargro et al. | 210/656 |
| 6,240,790 B1 | 6/2001 | Swedberg et al. | 73/863.21 |
| 6,258,263 B1 | 7/2001 | Henderson et al. | 210/198.2 |
| 6,264,892 B1 | 7/2001 | Kaltenbach et al. | 422/68.1 |
| 6,296,771 B1 | 10/2001 | Miroslav | 210/656 |
| 6,312,888 B1 | 11/2001 | Wong et al. | 435/4 |
| 6,387,234 B1 | 5/2002 | Yeung et al. | 204/451 |
| 6,432,290 B1 | 8/2002 | Harrison et al. | 204/453 |
| 6,436,292 B1 | 8/2002 | Petro | 210/656 |
| 6,444,150 B1 | 9/2002 | Arnold | 264/69 |
| 6,444,461 B1 | 9/2002 | Knapp et al. | 435/283.1 |
| 6,461,515 B1 | 10/2002 | Safir et al. | 210/656 |
| 6,464,866 B2 | 10/2002 | Moon et al. | 210/198.2 |
| 6,485,069 B1 | 11/2002 | Anderson | 292/175 |
| 6,494,614 B1 | 12/2002 | Bennett et al. | 366/336 |
| 6,497,138 B1 | 12/2002 | Abdel-Rahman et al. | 73/23.42 |
| 6,527,890 B1 | 3/2003 | Briscoe et al. | 156/89.11 |
| 6,537,506 B1 | 3/2003 | Schwalbe et al. | 422/130 |
| 6,551,839 B2 | 4/2003 | Jovanovich et al. | 436/180 |
| 6,581,441 B1 | 6/2003 | Paul | 73/61.52 |
| 6,623,860 B2 | 9/2003 | Hu et al. | 428/411.1 |
| 6,627,433 B2 | 9/2003 | Frazier et al. | 435/288.7 |
| 6,645,377 B1 | 11/2003 | Egorov et al. | 210/198.2 |
| 6,660,149 B1 | 12/2003 | Karger et al. | 204/601 |
| 6,663,697 B1 | 12/2003 | Kottenstette et al. | 96/101 |
| 6,664,104 B2 | 12/2003 | Pourahmadi et al. | 435/288.6 |
| 6,743,356 B1 | 6/2004 | Fermier et al. | 210/198.2 |
| 6,749,749 B2 | 6/2004 | Xie et al. | 210/198.2 |
| 6,812,030 B2 | 11/2004 | Ozbal et al. | 436/50 |
| 6,814,859 B2 * | 11/2004 | Koehler et al. | 210/198.2 |
| 2002/0017484 A1 | 2/2002 | Dourdeville | 210/198.2 |
| 2002/0048536 A1 | 4/2002 | Bergh et al. | 422/130 |
| 2002/0094533 A1 | 7/2002 | Hess et al. | 435/6 |
| 2002/0158022 A1 | 10/2002 | Huang et al. | 210/656 |
| 2002/0160139 A1 | 10/2002 | Huang et al. | 428/36.9 |
| 2002/0199094 A1 | 12/2002 | Strand et al. | 713/150 |
| 2003/0092056 A1 | 5/2003 | Nagasawa | 435/6 |
| 2003/0094415 A1 | 5/2003 | Tanimura | 210/656 |
| 2003/0118486 A1 | 6/2003 | Zhou et al. | 422/102 |
| 2003/0230524 A1 | 12/2003 | Soga et al. | 210/198.2 |
| 2004/0020834 A1 | 2/2004 | Mincsovics et al. | 210/198.2 |
| 2004/0084375 A1 | 5/2004 | Hodgin et al. | 210/656 |
| 2004/0134845 A1 | 7/2004 | Paul et al. | 210/198.2 |

OTHER PUBLICATIONS

Khandurina, Julia et al., *Microfabricated Porouos Membrane Structure for Sample Concentration and Electrophoretic Analysis*, "Analytical Chemistry," vol. 71, No. 9, May 1, 1999, pp. 1815–1819.

Poole, Colin F., "4.5 Column Preparation," *The essence of chromatography*, 2003 Elsevier Science B.V., Amsterdam, The Netherlands, pp. 393–401.

Poole, Colin F., "5.6 Coupled–Column Systems," *The essence of chromatography*, 2003 Elsevier Science B. V., Amsterdam, The Neterlands, pp. 451–455.

Poole, Colin F., "8.4.2 Column Technology," *The essence chromatography*, 2003 Elesevier Science B.V., Amsterdam, The Netherlands, pp. 664–668.

Krull, Ira S. et al., "2.3 Techniques for Packing Capillaries," *Capillary Electrochromatography and Pressurized Flow Capillary Electrochromatography*, 2000 HNB Publishing, New York, NY, pp. 40–46.

"Multi–Parallel–HPLC," Web document published at: http//www.sepiatec.com/download/phplc.pdf, SEPIAtec GmbH, Louis–Blériot–Strasse 5 D–12487 Berlin Germany.

Ericson, Christer, et al., *Electroosmosis– and Pressure–Driven Chromatography in Chips Using Continuous Beds*, "Analytical Chemistry," vol. 72, No. 1, Jan. 1, 2000.

MacNair, John E., et al., *Ultrahigh–Pressure Reversed–Phase Liquid Chromatography in Packed Capillary Columns*, "Analytical Chemistry," vol. 69, No. 6, Mar. 15, 1997, pp. 983–989.

MacNair, John E., et al., *Ultrahigh–Pressure Reversed–Phase Capillary Liquid Chromatography: Isocratic and Gradient Elution Using Columns Packed with 1.0–μm Particles*, "Analytical Chemistry," vol. 71, No. 3, Feb. 1, 1999, pp. 700–708.

Ocvirk, Gregor, et al., *High Performance Liquid Chromatography Partially Integrated onto a Silicon Chip*, "Analytical Methods and Instrumentation," vol. 2, No. 2, 1995, pp. 74–82.

Shelly, Dennis C., et al., *Insights into the Slurry Packing and Bed Structure of Capillary Liquid Chromatographic Columns*, "Journal of Chromatography," 458, Elsevier Science Publishers B.V., Amsterdam, The Netherlands, (1989), pp. 267–279.

Poole, Colin F., et al., *Chromatography today*, 1991, Elsevier Science Publishers B.V., Amsterdam, The Netherlands.

Keller, H.P., et al., *Dynamic Slurry–Packing Technique for Liquid Chromatography Columns*, "Analytical Chemistry," vol. 49, No. 13, Nov. 1977, pp. 1958–1963.

Southan, Christopher, SmithKline Beecham Pharmaceuticals, "Fast, Sensitive, Flexible, and Cheap: How to Make Your Own High–Speed Microbore Columns," Sep. 21, 1996, The Association of Biomolecular Resource Facilities, www.abrf.org.

Applied Biosystems, "POROS® HP Glass Columns for Preparative Chromatography," Aug. 2001.

Guček, Marjan, et al., *Separation of Sugar Anomers by Capillary Electrochromatography*, "Acta Chim. Slov.," Mar. 2, 2000, 47, 165–177.

Palm, Anders, et al., "Integrated Sample Preparation and MALDI MS on a disc," *Micro Total Analysis Systems*, J.M. Ramsey and A. van den Berg (eds.), 2001 Kluwer Academic Publishers, The Netherlands, pp. 216–218.

Zhang, Bailin, et al., *High–Throughput Microfabricated CE/ESI–MS: Automated Sampling from a Microwell Plate*, "Analytical Chemistry," vol. 73, No. 11, Jun. 1, 2001, pp. 2675–2681.

Manz, Andreas, et al., "Planar Chips Technology for Miniaturization of Separation Systems: A Developing Perspective in Chemical Monitoring," *Advances in Chromatography*, vol. 33, 1993 Dekker, Inc., New York/Basel/Hong Kong, pp. 1–66.

Manz, Andreas, et al., *Miniaturization f Separation Techniques Using Planar Chip Technology*, "Journal of High Resolution Chromatography," vol. 16, Jul. 1993, pp. 433–436.

Huber, Christian G., et al., *High–resolution liquid chromatography of DNA fragments on non–porous poly(styrene–divinylbenzene)particles*, "Nucleic Acids Research," 1993, vol. 21, No. 5, pp. 1061–1066.

Finot, Michael, et al., "High Throughput Pharmaceutical Formulation Evaluation and Analysis using Capillary Electrochromatography on a Microfluidic Chip," *Micro Total Analysis Systems*, J.M. Ramsey and A. van den Berg (eds.), 2001 Kluwer Academic Publishers, The Netherlands, pp. 480–482.

Jemere, Abedaw B., et al., "Microchip–Based Selective Preconcentration using Protein A Immunoaffinity Chromatography," *Micro Total Analysis Systems*, J.M. Ramsey and A. van den Berg (eds.), 2001 Kluwer Academic Publishers, The Netherlands, pp. 501–502.

Morishima, Keisuke, et al., "In–Situ Preparation of Photopolymerized Sol–Gel Monoliths for Capillary Electrochromatography on a Chip," *Micro Total Analysis Systems*, J.M. Ramsey and A. van den Berg (eds.), 2001 Kluwer Academic Publishers, The Netherlands, pp. 557–558.

Seki, Minoru, et al., "Chromatograhic Separation of Proteins on a PDMS–Polymer Chip by Pressure Flow," *Micro Total Analysis Systems*, J.M. Ramsey and A. van den Berg (eds.), 2001 Kluwer Academic Publishers, The Netherlands, pp. 48–50.

Sato, Kiichi; et al., "Integrated Immunoassay System using Multichannel Microchip for Simultaneous Determination," *Micro Total Analysis Systems*, J.M. Ramsey and A. van den Berg (eds.), 2001 Kluwer Academic Publishers, The Netherlands, pp. 511–512.

* cited by examiner

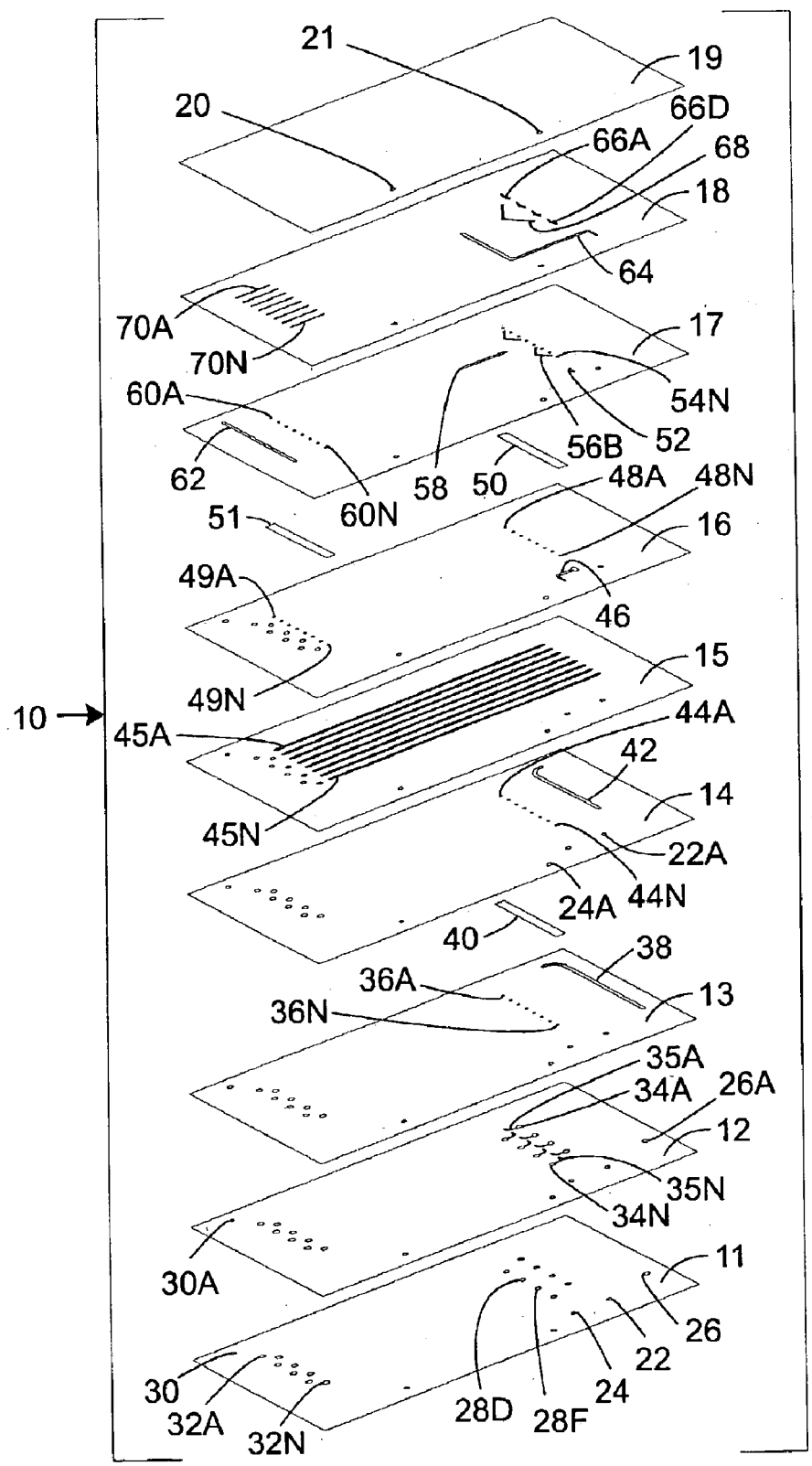
FIG._1A

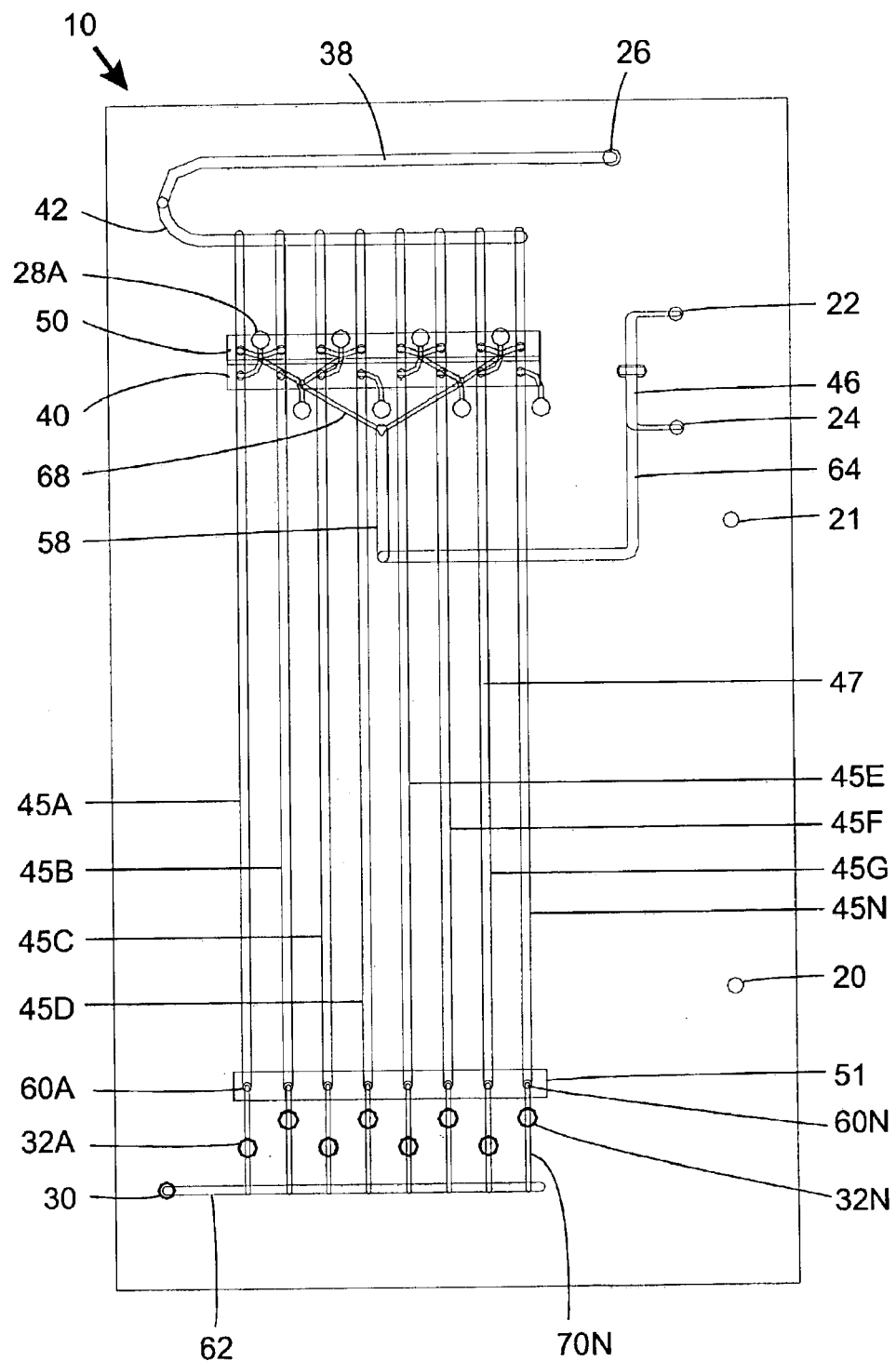
FIG._1B

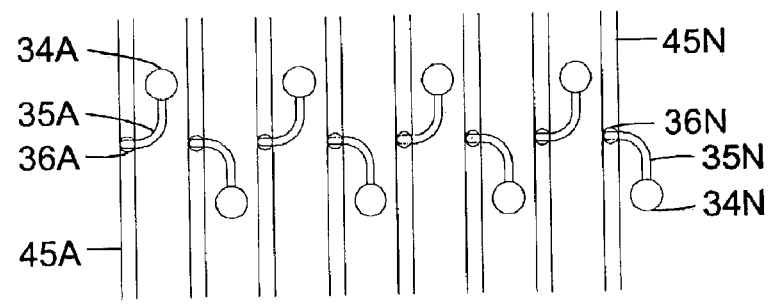
FIG._1C
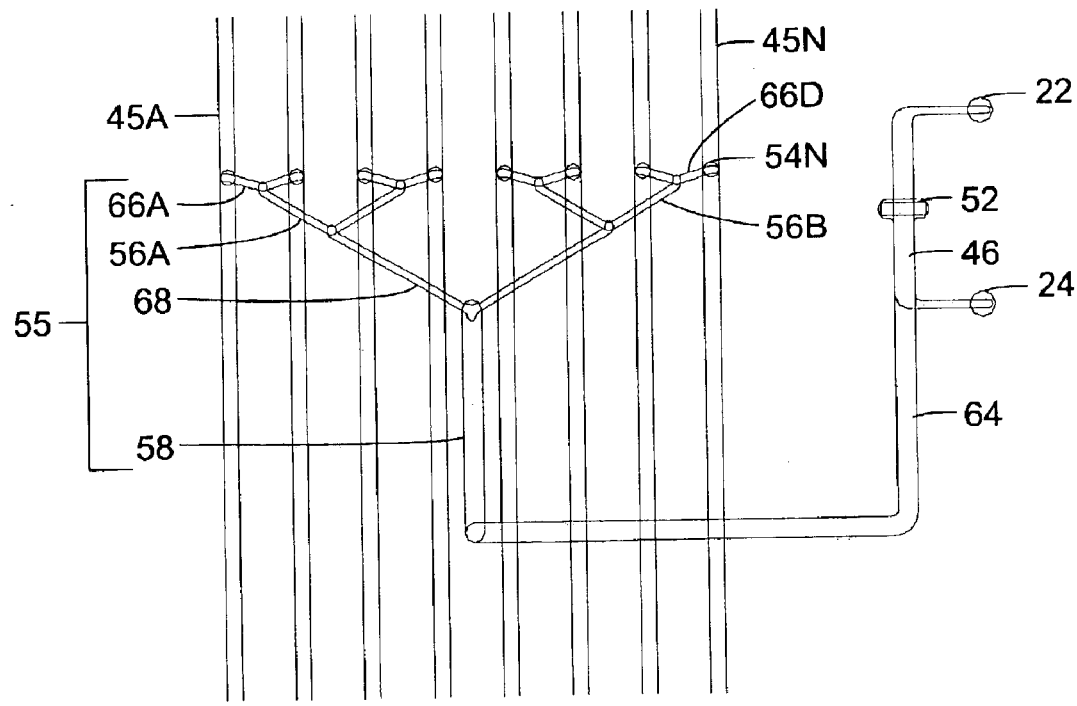
FIG._1D

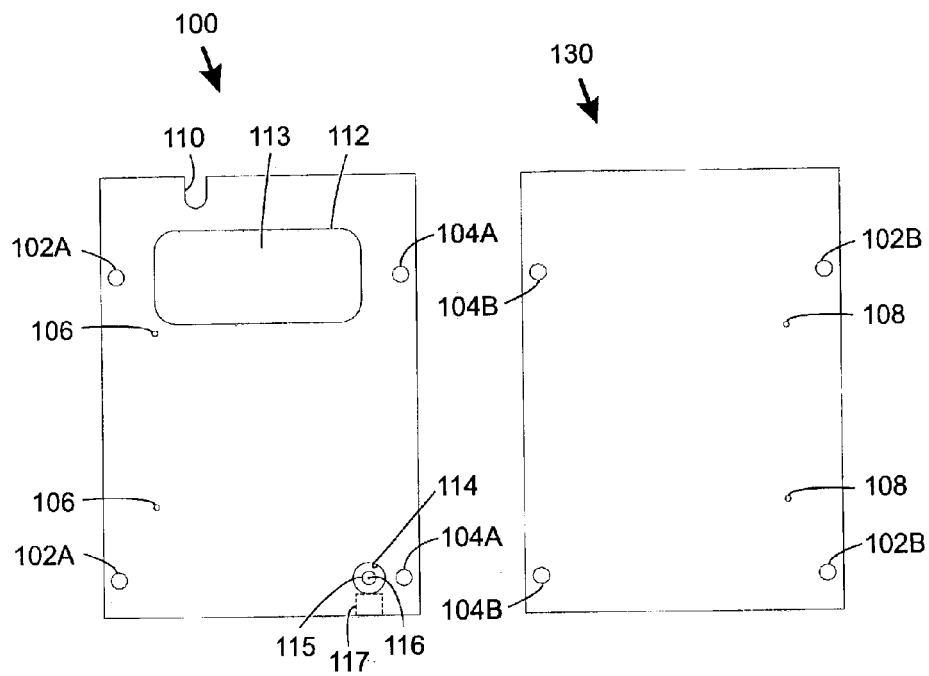
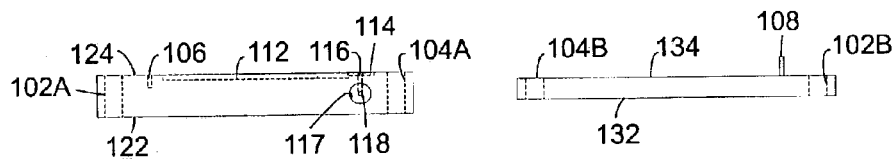
FIG._2C  FIG._2D

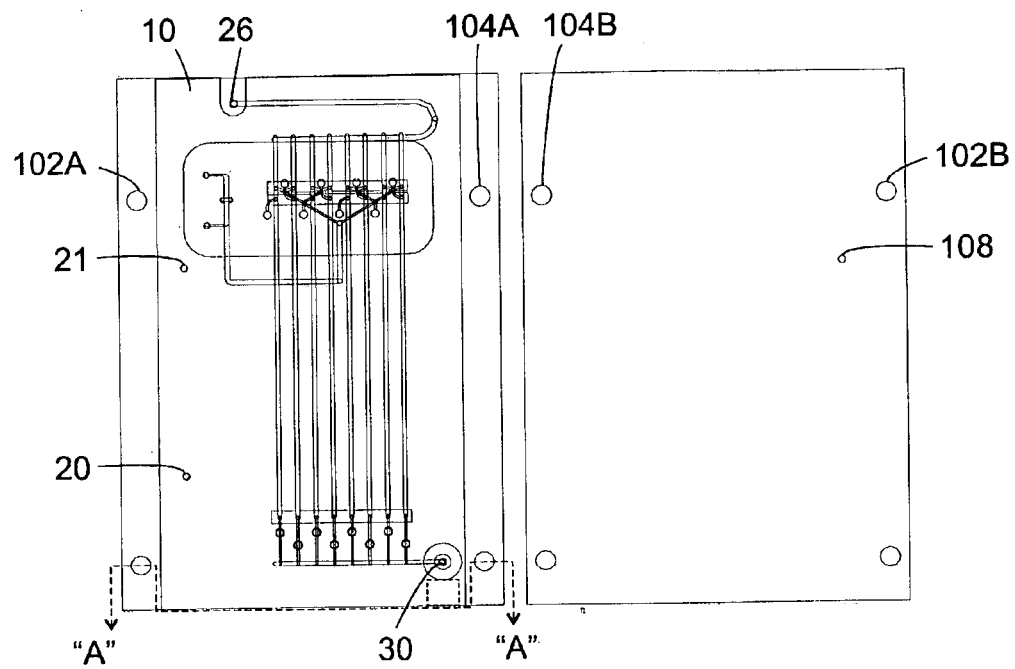
FIG._2E
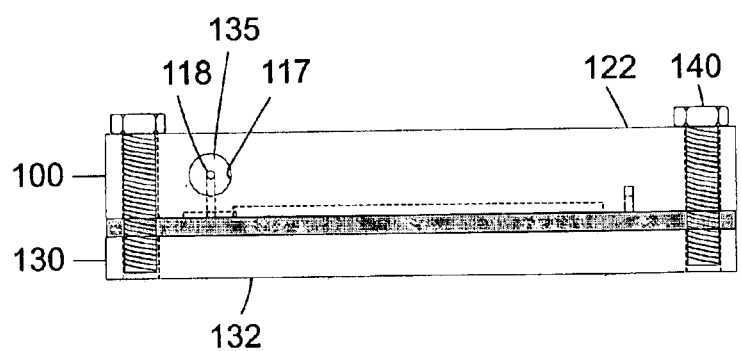
FIG._2F

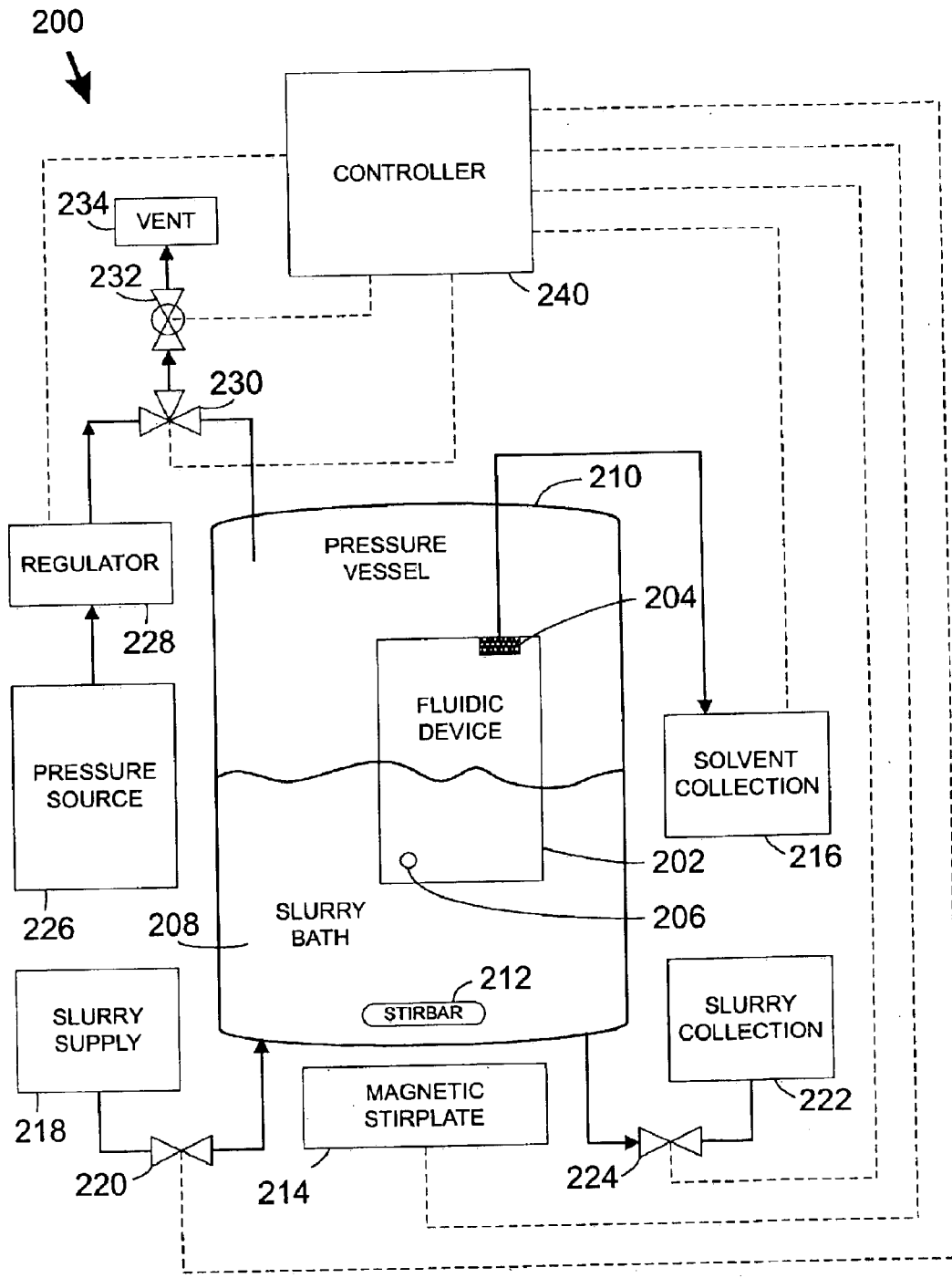
FIG._3

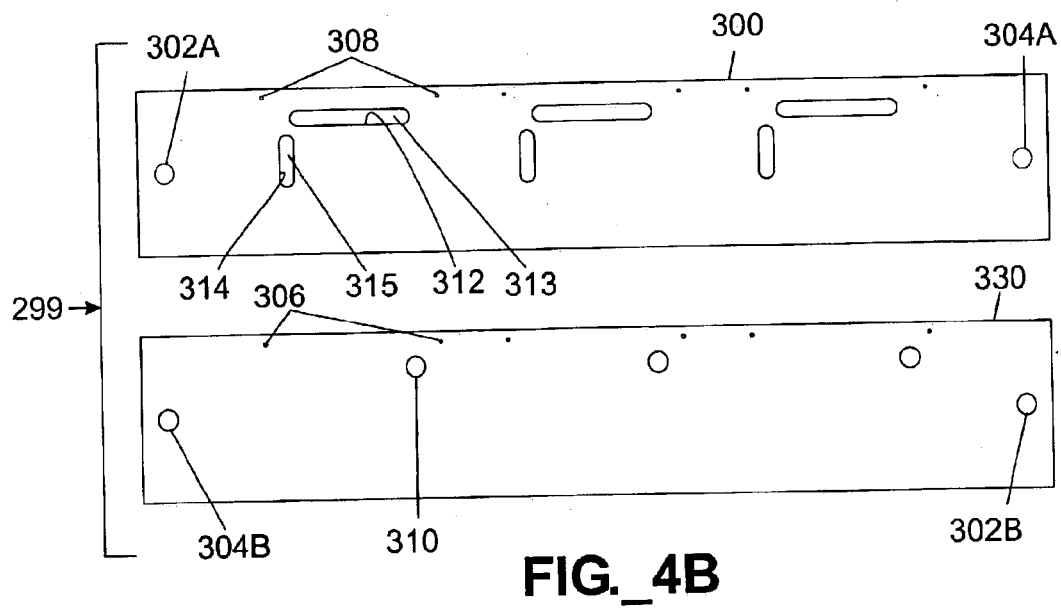
FIG._4B
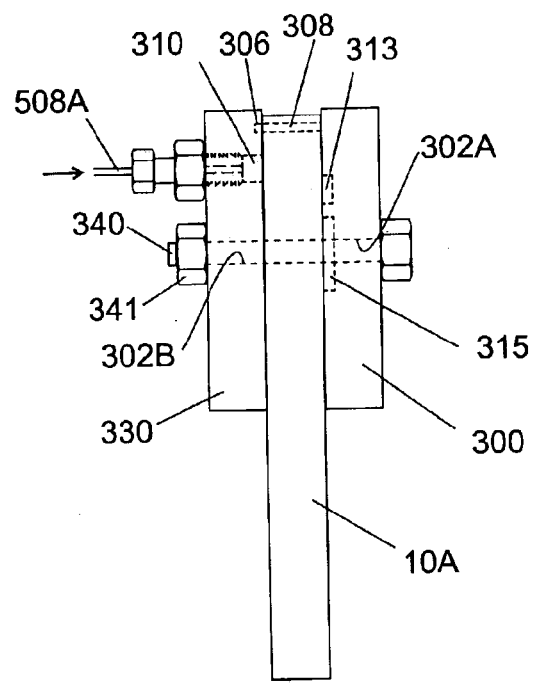
FIG._4A

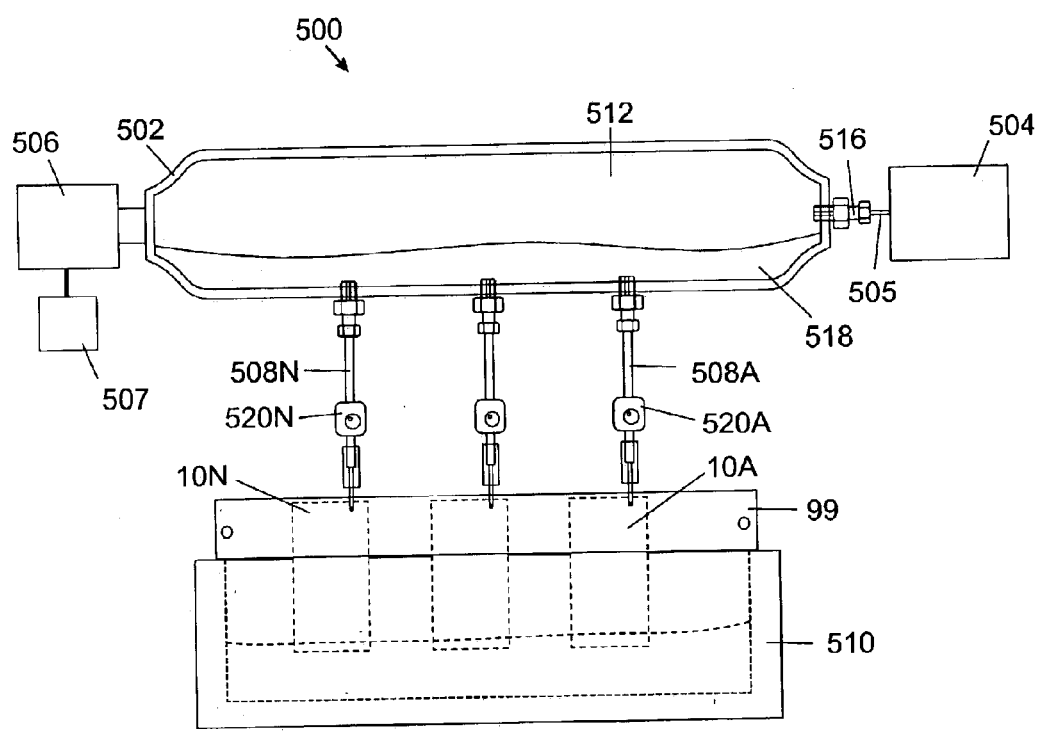
FIG._5A

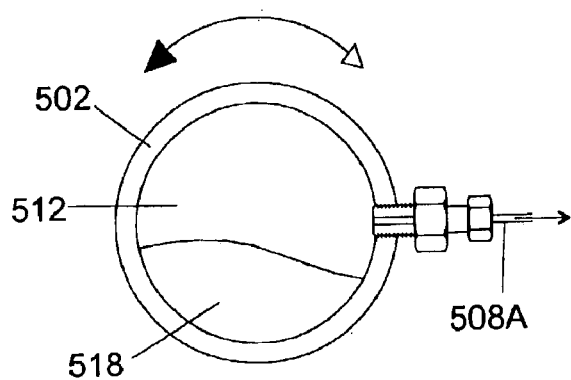
FIG._5C
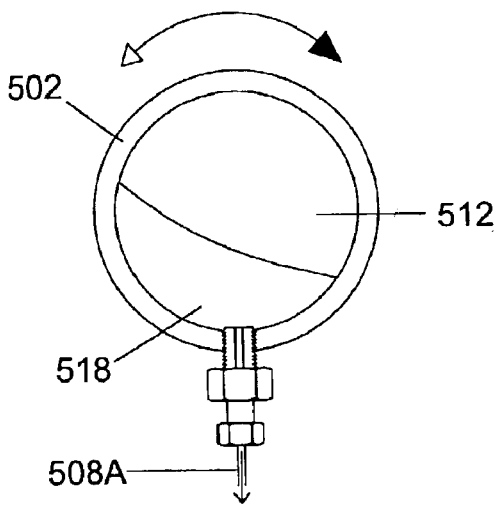
FIG._5B

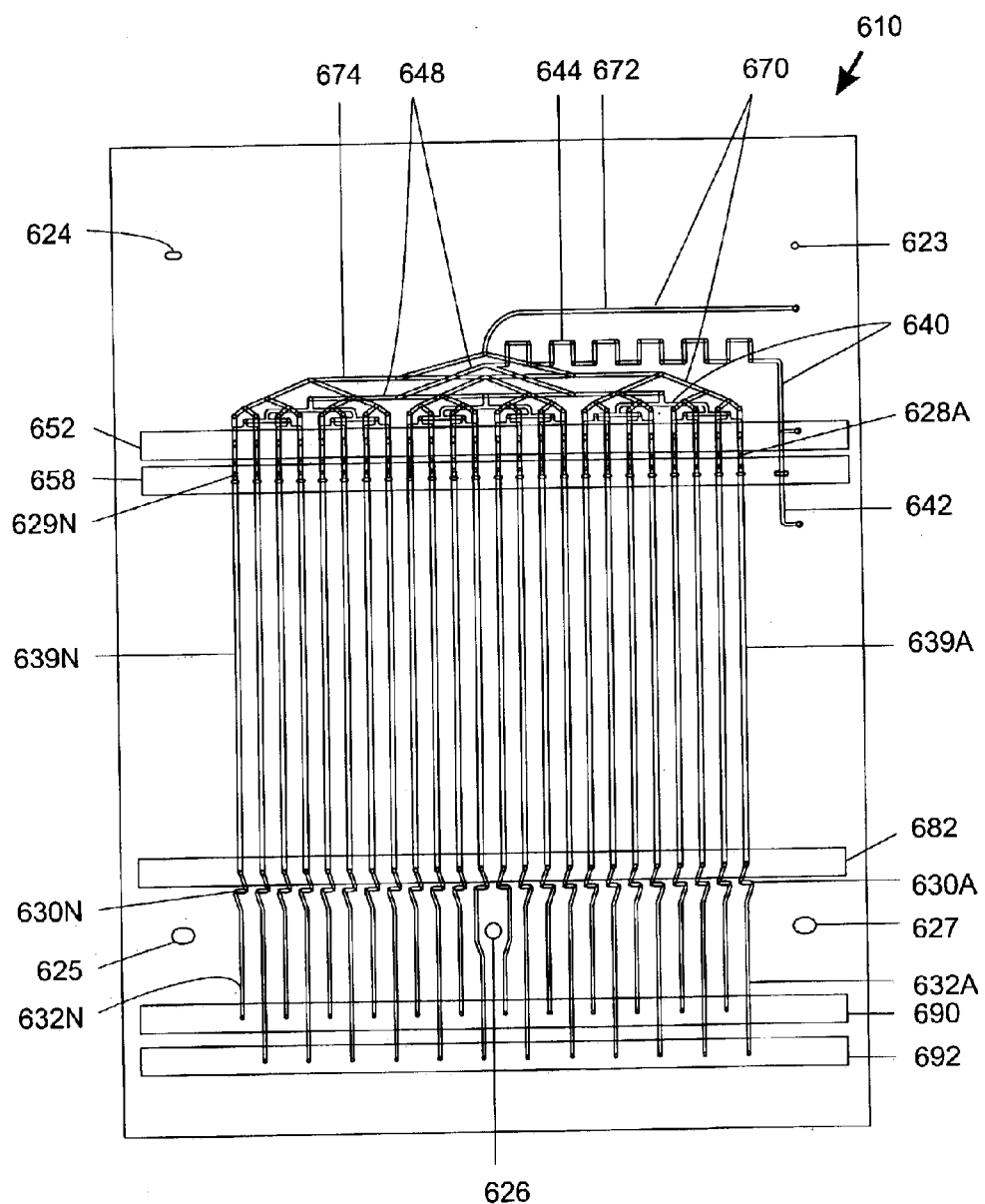
FIG._6

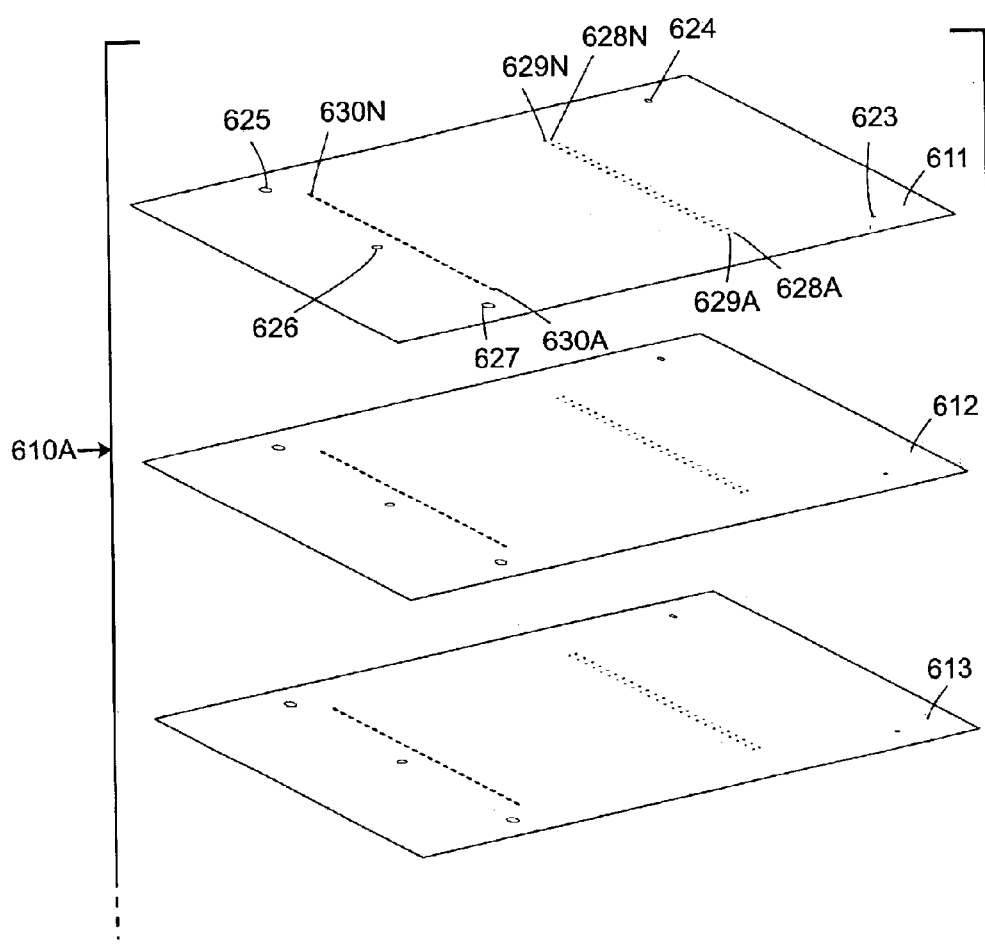
FIG._7A

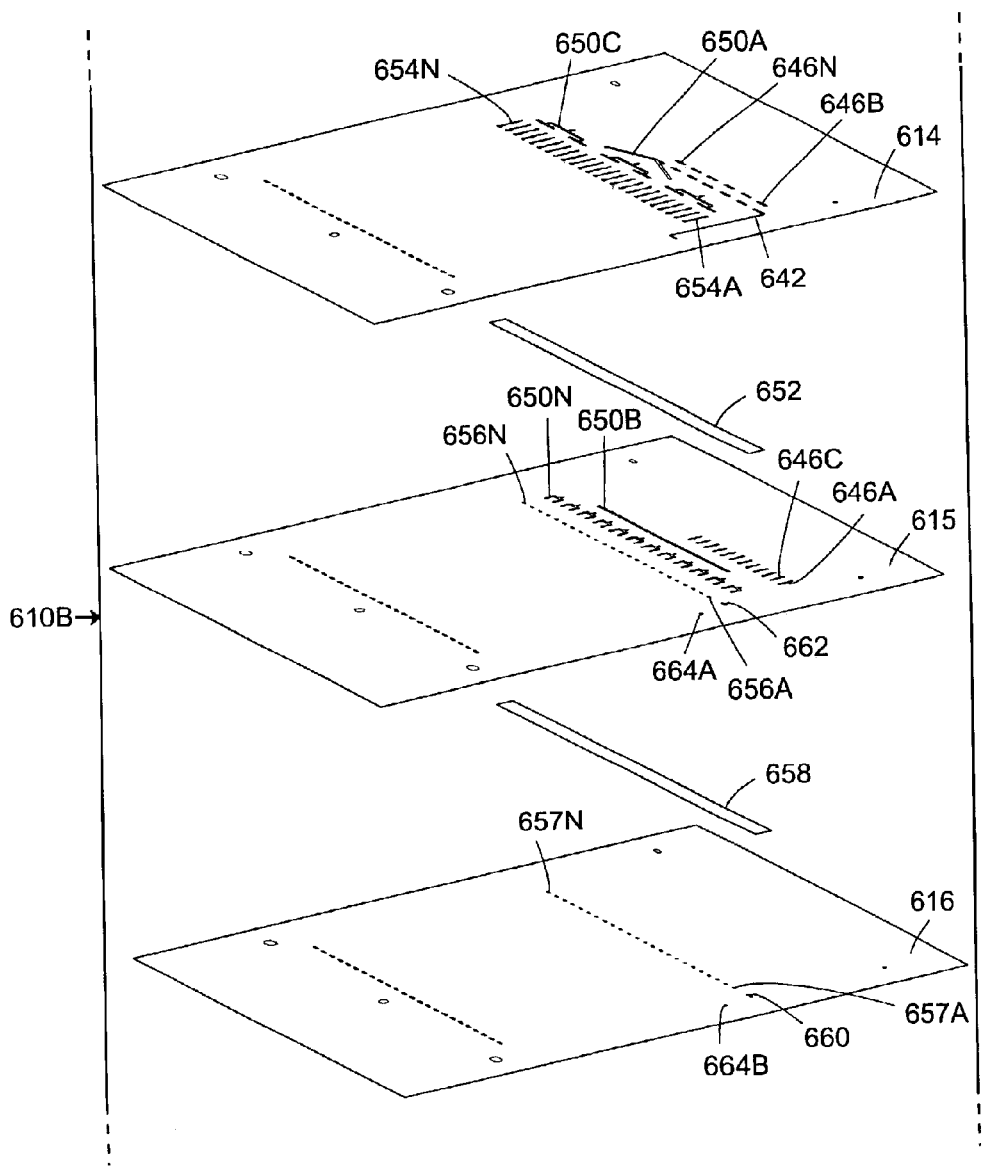
FIG._7B

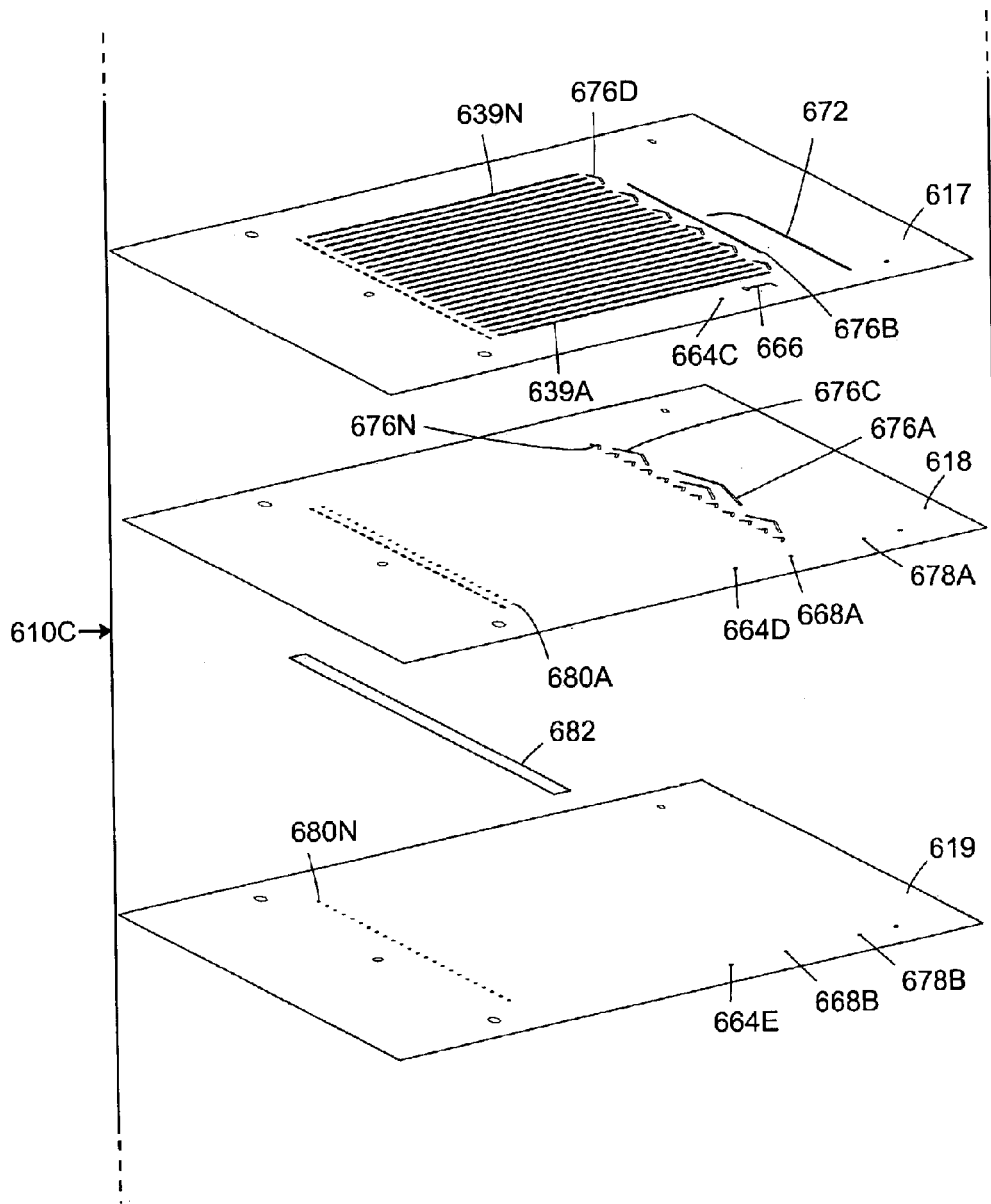
FIG._7C

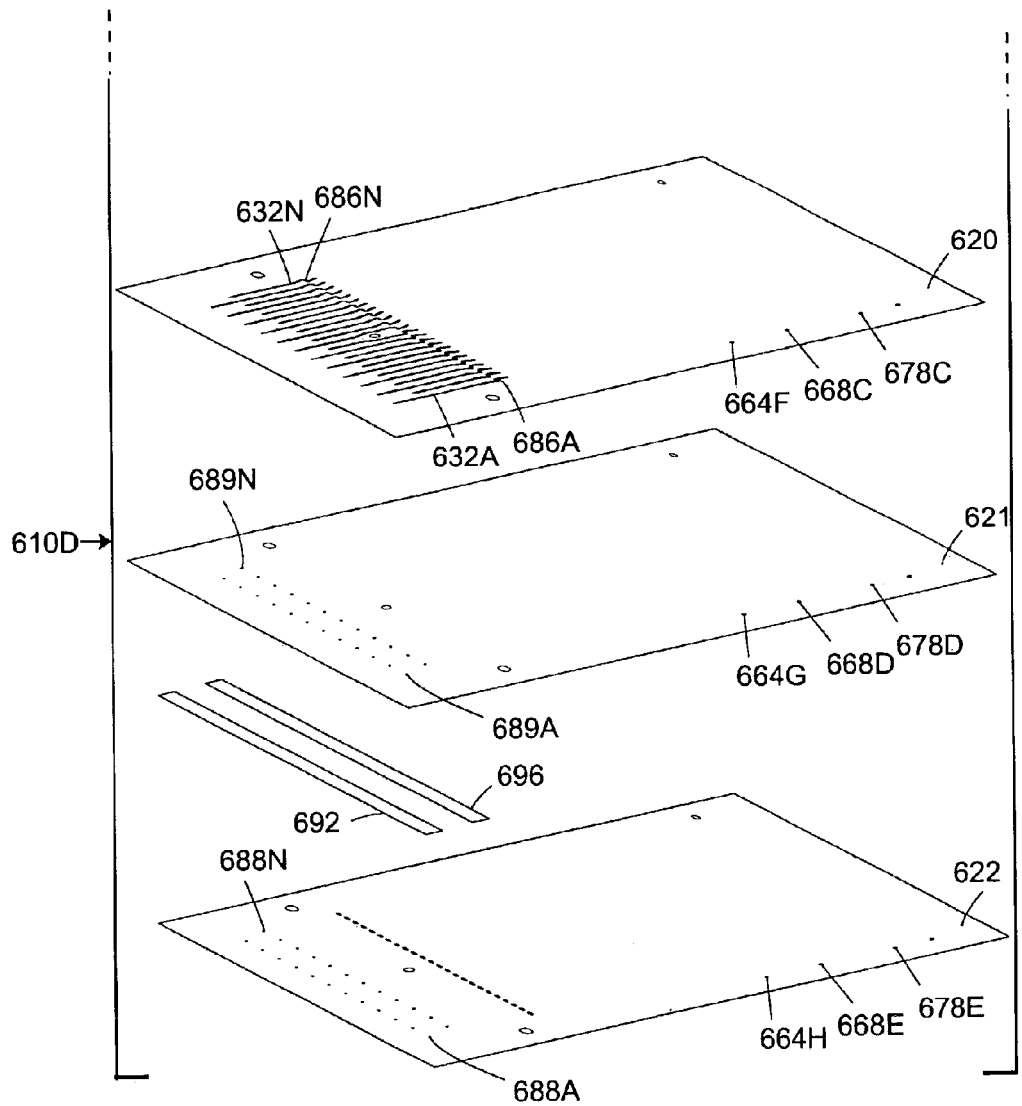
FIG._7D

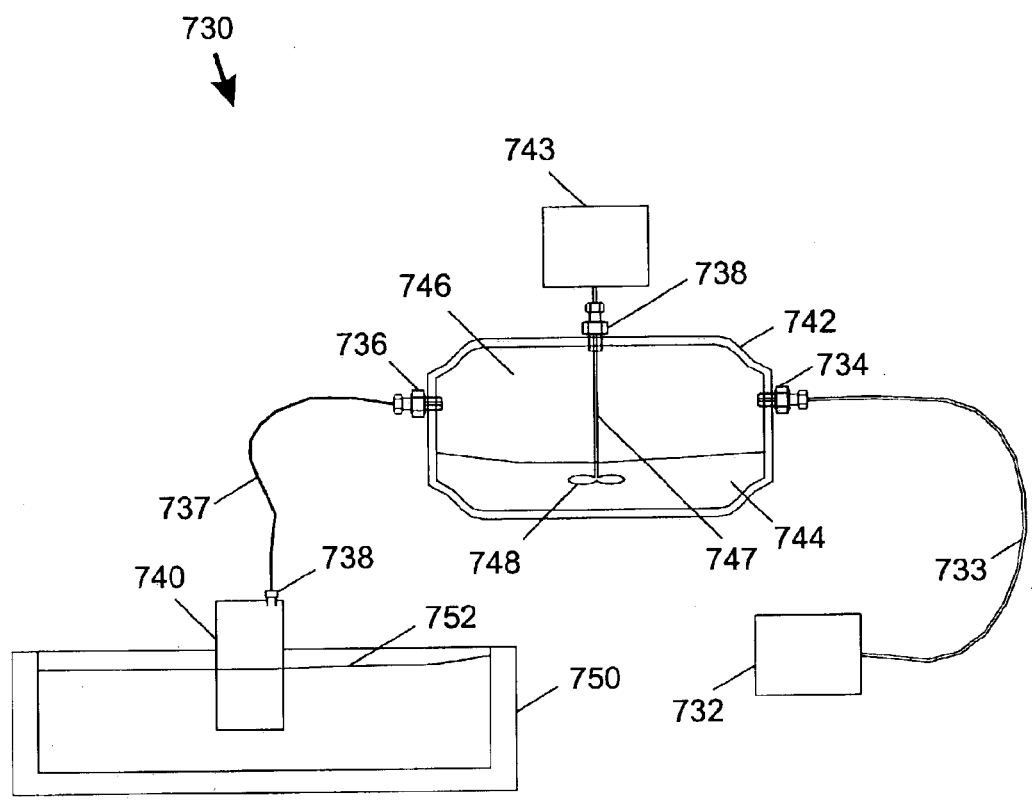
FIG._9

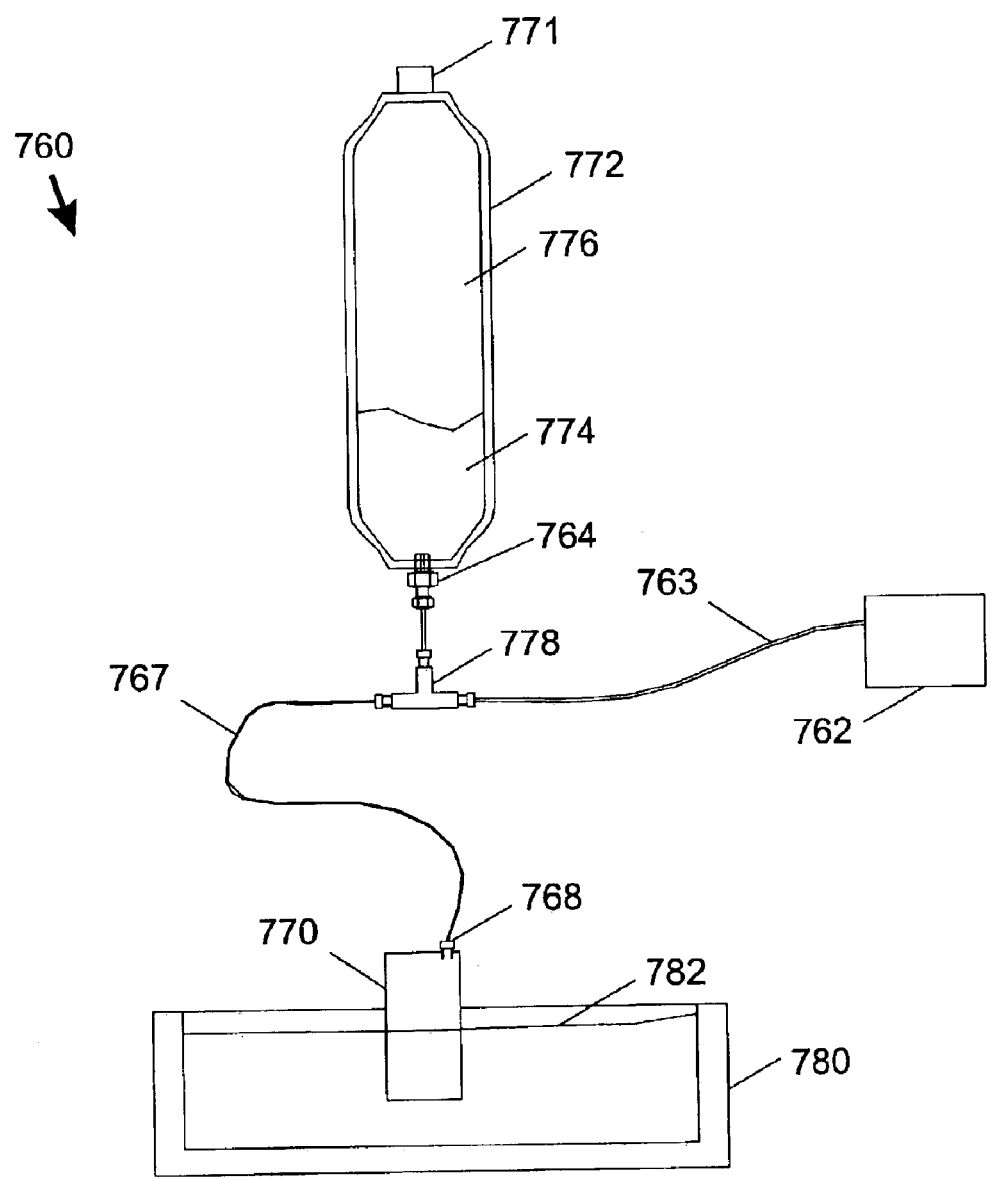
FIG._10

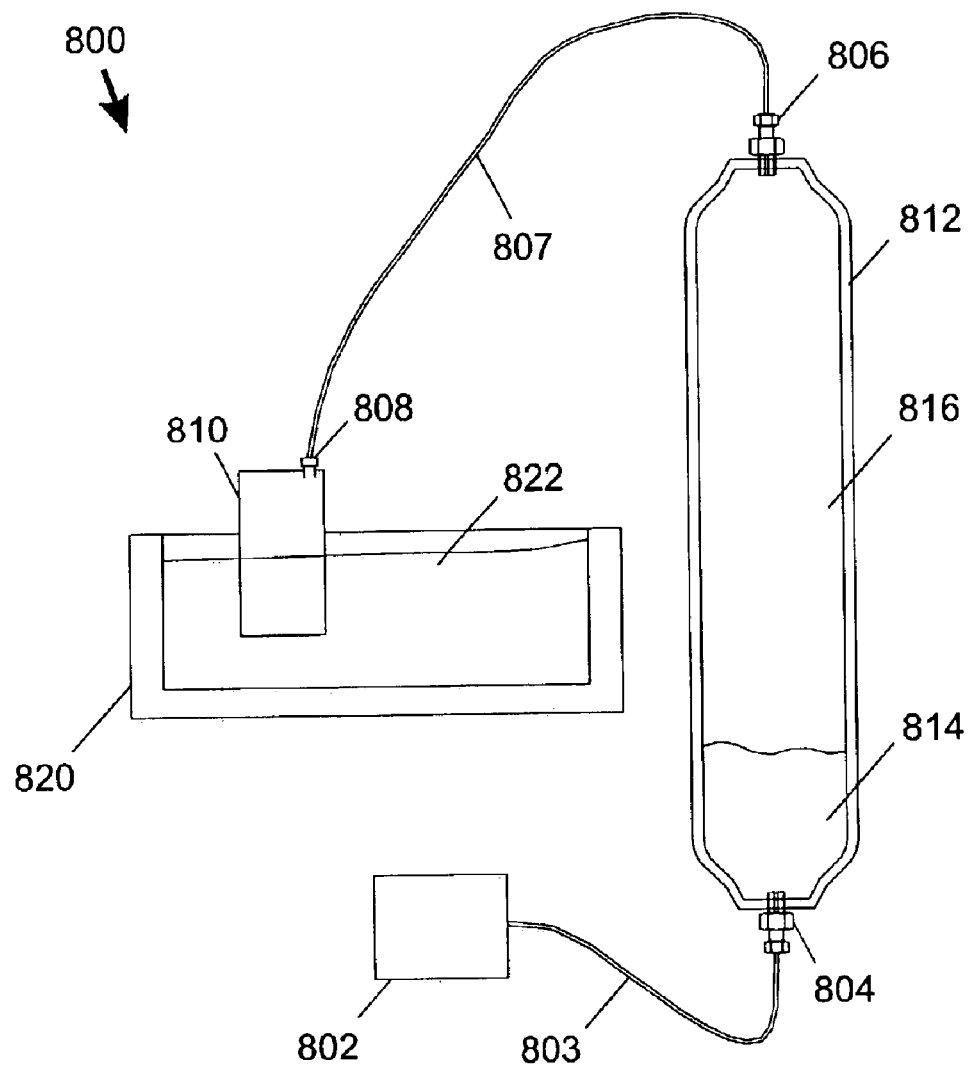
FIG._11

SEPARATION COLUMN DEVICES AND FABRICATION METHODS

STATEMENT OF RELATED APPLICATION(S)

This application claims benefit of two commonly assigned U.S. Provisional Patent Applications, Ser. No. 60/357,683 filed Feb. 13, 2002 and Ser. No. 60/415,896 filed Oct. 3, 2002.

FIELD OF THE INVENTION

The present invention relates to the fabrication of separation columns such as may be used for separating chemical or biological species.

BACKGROUND OF THE INVENTION

Chemical and biological separations are routinely performed in various industrial and academic settings. One technique for performing such separations, chromatography, encompasses a number of methods that are used for separating closely related components of mixtures. In fact, chromatography has many applications including separation, identification, purification, and quantification of compounds within various mixtures. Chromatography is a physical method of separation wherein components typically partition between two phases: a stationary phase and a mobile phase. Sample components are carried by a mobile phase through a bed of stationary phase.

In column chromatography, the stationary phase refers to a coating on a solid support that is typically contained within a tube or other boundary. The mobile phase is forced by gravity or a pressure differential through the stationary phase. The mobile phase acts as a carrier for a sample solution. As the sample solution flows with the mobile phase through the stationary phase, the components of that solution will migrate according to interactions with the stationary phase and are retarded to varying degrees. The time a particular compound spends in the stationary phase relative to the fraction of time spent in the mobile phase will determine its velocity through the column.

Separation columns may be packed in several different ways, although conventional methods for packing such columns are typically slow and difficult. A simple packing method is to dry-pack an empty tube by shaking particles down with the aid of vibration from a sonicator bath or an engraving tool. A cut-back pipette tip may be used as a reservoir at the top, and the tube to be packed is plugged with parafilm or a tube cap at the bottom. The dry-packed tube may then be secured at the bottom end with a ferrule, frit, and male nut, and at the top end with the same fittings, minus the frit. The tube contents may be further compressed by flowing pressurized solvent through the packing material. When compacting of the particle bed has ceased and the fluid pressure has stabilized, the tubing is cut down to the bed surface, and then reassembled before use.

Another packing method utilizes slurry. An empty column is attached to a packing reservoir such as a Poros® Self-Pack® reservoir (PerSeptive Biosystems, Foster City, Calif.) upon which the column is filled with an appropriate amount of dilute slurry. The end of the reservoir column is then screwed on firmly before the tube is internally pressurized with a fluid and an appropriate instrument such as a pump. Pressures of several hundreds or even thousands of pounds per square inch (psi) may be applied, depending on the material properties of the tubing and the ability to seal the apparatus from leakage. Typically, a packed tube is cut following the packing step to remove any dead volume (where packing is incomplete or not present), to remove any contaminated regions, and/or to yield multiple sections of desired length. Thereafter, fittings are added to each tube sections to permit interface with other fluidic components such as pumps.

The foregoing packing methods have drawbacks that limit their utility. To begin with, such methods are relatively slow and inefficient. Conventional dry packing and slurry packing methods typically require tubing to be cut or trimmed, and then fitted with fittings for connecting to other components. These steps are labor-intensive, and the presence of additional fittings presents potential leakage problems during operation. Additionally, conventional slurry-packing methods are plagued with notorious blockage problems, especially when applied to small-bore columns such as capillaries. Such blockage or clogging during the packing step can prevent a column from being packed completely, if at all.

Also, it may be desirable to include multiple separation columns in a single device, such as a microfluidic device. Such an arrangement would allow high throughput analysis of samples by analyzing multiple samples in parallel. Conventional packing methods, however, are not capable of packing multiple separation columns simultaneously. Moreover, it may be desirable to pack several such microfluidic devices simultaneously to permit the fabrication of large numbers of such devices.

In light of the foregoing, there exists a need for improved column packing methods. It would be desirable to provide multiple separation columns on a single device, such as a multi-column microfluidic separation device, and to provide methods for fabricating such devices. It also would be desirable to provide packing methods that may be easily scaled up to permit fabrication of separation devices in large quantities.

BRIEF DESCRIPTION OF THE DRAWINGS

FIG. 1A is an exploded perspective view of a nine-layer microfluidic separation device containing eight separation columns.

FIG. 1B is a top view of the assembled device of FIG. 1A.

FIG. 1C is an enlarged top view of a first portion of the separation device of FIGS. 1A–1B showing sample injection ports and associated channels.

FIG. 1D is an enlarged top view of a second portion of the separation device of FIGS. 1A–1B showing solvent inlet ports, a mixing region, and a splitting network for splitting and distributing a solvent mixture among eight columns.

FIG. 2A is bottom view of a first (upper) plate of a first clamp assembly that may be used to assist in packing columns of the device illustrated in FIGS. 1A–1B.

FIG. 2B is a top view of a second (lower) plate of the same clamp assembly. FIG. 2C is an end view of the first plate illustrated in FIG. 2A.

FIG. 2D is an end view of the second plate illustrate in FIG. 2B.

FIG. 2E shows the first plate and the second plate of FIGS. 2A–2B with the microfluidic device illustrated in FIGS. 1A–1B superimposed over the first plate.

FIG. 2F is a composite sectional view along section lines "A"—"A" (shown in FIG. 2E) of the clamp assembly, including the first plate and the second plate illustrated in the preceding figures, bolted and clamped around the microfluidic device illustrated in FIGS. 1A–1D.

FIG. 3 is a schematic illustration of a system and apparatus for packing at least one separation column.

FIG. 4A is a side view of the device of FIGS. 1A–1B positioned in a second clamp assembly mechanism used to pack the separation columns of the device.

FIG. 4B is an exploded front view of the clamping mechanism of FIG. 4A.

FIG. 5A is a schematic illustration of a system utilizing a rotatable cylinder for packing at least one separation column.

FIG. 5B is a schematic illustration of a cross section of a portion of the system of FIG. 5A depicting the cylinder in a first rotational position.

FIG. 5C is a schematic illustration of a cross section of a portion of the system of FIG. 5A depicting the cylinder in a second rotational position.

FIG. 6 is a top view of a multi-layer microfluidic device containing twenty-four separation columns.

FIG. 7A is an exploded perspective view of a first portion, including the first through third layers, of the microfluidic device shown in FIG. 6.

FIG. 7B is an exploded perspective view of a second portion, including the fourth through sixth layers, of the microfluidic device shown in FIG. 6.

FIG. 7C is an exploded perspective view of a third portion, including the seventh-through ninth layers, of the microfluidic device shown in FIG. 6.

FIG. 7D is an exploded perspective view of a fourth portion, including the tenth through twelfth layers, of the microfluidic device shown in FIG. 6.

FIG. 9 is a schematic illustration of a system utilizing a mechanically stirred cylinder for packing at least one separation column.

FIG. 10 is a schematic illustration of a system utilizing a gravity fed flowing stream for packing at least one separation column.

FIG. 11 is a schematic illustration of a system utilizing a fluidized bed for packing at least one separation column.

DETAILED DESCRIPTION OF PREFERRED EMBODIMENTS OF THE INVENTION

Definitions

Figure 7E:
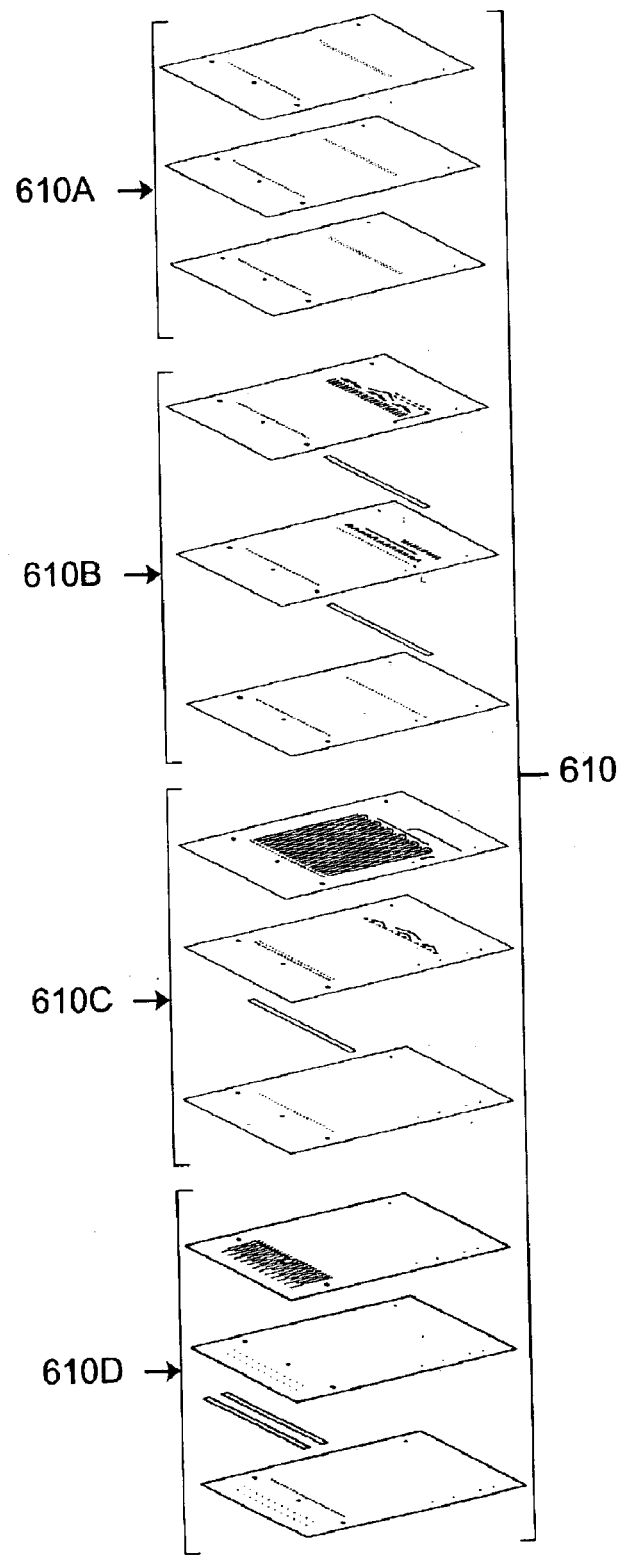
FIG. 7E is a reduced size composite of FIGS. 7A–7D showing an exploded perspective view of the microfluidic device of FIG. 6.

The term "column" as used herein refers to a region of a fluidic device containing stationary phase material, typically including packed particulate matter. In microfluidic devices described herein, the term "column" is used synonymously with a packed separation channel.

The term "microfluidic" as used herein refers to structures or devices through which one or more fluids are capable of being passed or directed and having at least one dimension less than about 500 microns.

The term "pressure vessel" as used herein refers to a vessel that is substantially sealed against unintended leakage and is capable of being pressurized to a pressure that is significantly greater-than-atmospheric pressure.

The term "slurry" as used herein refers to a mixture of particulate matter and a solvent, preferably a suspension of particles in a solvent.

The term "stencil" as used herein refers to a material layer or sheet that is preferably substantially planar through which one or more variously shaped and oriented portions have been cut or otherwise removed through the entire thickness of the layer, and that permits substantial fluid movement within the layer (e.g., in the form of channels or chambers, as opposed to simple through-holes for transmitting fluid through one layer to another layer). The outlines of the cut or otherwise removed portions form the lateral boundaries of microstructures that are formed when a stencil is sandwiched between other layers such as substrates and/or other stencils.

Fluidic Devices Generally

Column fabrication methods according to the present invention may be applied to various types of fluidic devices, including devices utilizing one or more conventional-scale tubes, capillary tubes, or microfluidic channels. In an especially preferred embodiment, fluidic devices are constructed using stencil layers or sheets to define channels and/or other microstructures. For example, a computer-controlled plotter modified to accept a cutting blade may be used to cut various patterns through a material layer. Such a blade may be used either to cut sections to be detached and removed from the stencil layer or to fashion slits that separate certain regions of a layer without removing any material. Alternatively, a computer-controlled laser cutter may be sued to cut portions through a material layer. While laser cutting may be used to yield precisely-dimensioned microstructures, the use of a laser to cut a stencil layer inherently involves the removal of some material. Further examples of methods that may be employed to form stencil layers include conventional stamping or die-cutting technologies. The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers are intended to mate with one or more adjacent layers (such as stencil layers or substrate layers) to form a substantially enclosed device, typically having at least one inlet port and at least one outlet port.

Various means may be used to seal or bond layers of a device together. For example, adhesives may be used. In one embodiment, one or more layers of a device may be fabricated from single- or double-sided adhesive tape, although other methods of adhering stencil layers may be used. A portion of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thicknesses of these carrier materials and adhesives may be varied.

In another embodiment, device layers may be directly bonded without using adhesives to provide high bond strength (which is especially desirable for high-pressure applications) and eliminate potential compatibility problems between such adhesives and solvents and/or samples. Desirable operating pressures are preferably greater than about 10 psi (69 kPa), more preferably greater than about 100 psi (690 kPa), and more preferably still greater than about 400 psi (2.8 MPa). Specific examples of methods for directly bonding layers of unoriented polyolefins such as unoriented polypropylene to form stencil-based microfluidic structures are disclosed in co-pending U.S. patent application Ser. No. 10/313,231 (filed Dec. 6, 2002), which is owned by assignee of the present application and incorporated by reference as if fully set forth herein. In one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately 5 hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

In further embodiment, microfluidic devices for use with the methods according to the present invention may be fabricated from materials such as glass, silicon, silicon nitride, quartz, or similar materials. Various conventional machining or micromachining techniques such as those known in the semiconductor industry may be used to fashion channels, vias, and/or chambers in these materials. For example, techniques including wet or dry etching and laser ablation may be used. Using such techniques, channels chambers, and/or apertures may be made into one or more surfaces of a material or penetrate through a material.

Still further embodiments may be fabricated from various materials using well-known techniques such as embossing, stamping, molding, and soft lithography.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Preferred Fluidic Devices

In a preferred embodiment, a pressure-driven fluidic device includes multiple channels that may be packed to form separation columns sufficient for performing liquid chromatography. Preferably, such a device permits multiple different samples to be separated simultaneously using a minimum number of expensive system components such as pumps, pulse dampers, etc. For example, FIGS. 1A–1B illustrate a microfluidic separation device 10 including eight separation channels 45A–45N containing stationary phase material 47. (Although FIGS. 1A–1B show the device 10 having eight separation columns 45A–45N, it will be readily apparent to one skilled in the art that any number of columns 45A–45N may be provided. For this reason, the designation "N" represents a variable and could represent any desired number of columns. This convention is used throughout this document.) The device 10 may be constructed with nine substantially planar device layers 11–19, including multiple stencil layers 12–18. Each of the nine device layers 11–19 defines two alignment holes 20, 21, which are used in conjunction with external pins (not shown) to aid in aligning the layers 11–19 during construction, and/or to aid in aligning the device 10 with an external interface during a packing process.

The first device layer 11 defines several fluidic ports: two solvent inlet ports 22, 24 are used to admit (mobile phase) solvent to the device 10; eight sample ports 28A–28N permit sample to be introduced to eight columns (provided in channels 45); a slurry inlet port 26 is used during a column packing process to admit slurry to the device 10; and a fluidic outlet port 30 that is used [1] during the packing process to exhaust (slurry) solvent from the device 10; and [2] during operation of the separation device 10 to carry effluent from the device 10. Alternatively, multiple outlet ports (not shown) may be provided to separately transport the effluent stream from each separation channel 45A–45N off of the device 10. Due to the sheer number of elements depicted in FIGS. 1A–1B, numbers for selected elements within alphanumeric series groups (e.g., sample inlet ports 28A–28N are omitted from the drawings for clarity.

Each of the first through sixth layers 11–16 defines eight optical detection windows 32A–32N. Defining these windows 32A–32N through these device layers 11–16 facilitates optical detection by locally reducing the thickness of material bounding (from above and below) channel segments 70A–70N disposed downstream of the column-containing channels 45A–45N, thus reducing the amount of material between an external optical detector (not shown) such as a conventional UV-VIS detector, and the samples contained in the segments 70A–70N. Various types of optical detectors may be used to detect at least one property of a substance eluted from the packed separation channels 45A–45N.

The second through seventh layers 12–17 each define a first solvent via 22A for communicating a mobile phase solvent from a first mobile phase inlet port 22 to a first mobile phase channel 64 defined in the eighth layer 18, with further solvent vias 24A defined in the second through fifth layers 12–15 to transport a second mobile phase solvent to the channel 46 defined in the sixth layer 16. Additional vias 30A are defined in the second through sixth layers 12–16 to provide a fluid path between the fluidic port 30 and the effluent channel 62 defined in the seventh layer 17. A via 26A defined in the second layer 12 communicates slurry from the slurry inlet port 26 to a transverse channel 38 defined in the third layer 13 during a slurry packing process. Preferably, particulate material deposited by the slurry packing process fills not only the multiple separation channels 45A–45N, but also fills the channel 42 and at least a portion of the channel 38. The second layer 12 further defines eight sample channels 35A–35N each having an enlarged region 34A–34N aligned with a sample inlet port 28A–28N defined in the first layer 11.

In addition to the structures described previously, the third layer 13 defines an elongate channel 38, and eight sample vias 36A–36N each aligned with the ends of a corresponding sample channel 35A–35N. The fourth layer 14 defines a manifold channel 42 and eight sample vias 44A–44N aligned with the vias 36A–36N in the third layer 13. The manifold channel 42 that provides fluid communication with the separation channels 45 defined in the fifth layer 15 and the elongate channel 38 defined in the third layer 13. The separation channels 45 preferably are about 40 mils (1 mm) wide or smaller. As an alternative to the manifold channel 42, a junction with radiating segments (not shown) could be used.

A porous (sample) frit 40 is disposed between the third layer 13 and fourth layers 14. The function of this frit 40 is to retain stationary phase material 47 in the separation channels 45A–45N, yet permit the passage of fluid when desired (i.e., fluidic samples supplied to the device 10 through the sample ports 28A–28N). Although various frit materials may be used, the frit 40 (along with frits 50, 51) is preferably constructed from a permeable polypropylene membrane such as, for example, 1-mil thickness Celgard 2500 membrane (55% porosity, 0.209×0.054 micron pore size, Celgard Inc., Charlotte, N.C.), particularly if the layers 11–19 of the device 10 are bonded together using an adhesiveless thermal bonding method utilizing platens, such as described above. Preferably, the frit material has an average pore size that is smaller than the average particle size of the particulate to be packed within the device 10, so as to ensure that the packing material is retained within the device 10. Applicants have obtained favorable results using this specific frit material, without noticeable wicking or lateral flow within the frit despite using a single strip 40 of the frit membrane to serve multiple adjacent column-containing channels. As a less-preferred alternative to the single frit 40, multiple discrete frits (not shown) of various porous material types and thicknesses may be substituted.

The sixth layer 16 defines a channel 46 that communicates a second mobile phase solvent from vias 24A to the slit 52 defined in the seventh layer 17, which facilitates mixing of the two solvents in the channel 64 downstream of the slit 52. Further defined in the sixth layer 16 are eight vias 48A–48N for admitting mixed mobile phase solvent to the upstream ends of the separation channels 45A–45N, and a second set of eight vias 49A–49N at the downstream end of the same separation channels 45 for transporting effluent from the downstream ends of the separation channels 45A–45N. Two frits 50, 51 are placed between the sixth and the seventh layers 16, 17. The first (mobile phase solvent) frit 50 is placed immediately above the first set of eight vias 48A–48N, while the second (mobile phase+sample) frit 51 is placed immediately above the second set of eight vias 49A–49N and below a similar set of eight vias 60A–60N defined in the seventh layer 17. The seventh layer 17 defines a channel segment 58, two medium forked channel segments 68A–68B, and eight vias 54A–54N for communicating mobile phase solvent through the frit 50 and the vias 48A–48N to the separation channels 45 defined in the fifth layer 15. The seventh layer 17 further defines a downstream manifold channel 62 that receives mobile phase solvent and sample during separation, and that receives (slurry) solvent during column packing, for routing such fluids through vias 30A to the fluidic exit port 30 defined in the first device layer 11.

The eighth layer 18 defines a mixing channel 64, one large forked channel segment 68, and four small forked channel segments 66A–66D. The eighth layer 18 further defines eight parallel channel segments 70A–70N downstream of the frit 51 for receiving effluent during separation or solvent during slurry packing, and for transporting such fluid(s) to the manifold channel 62 defined in the seventh layer 17. The ninth layer 19 serves as a cover for the channel structures defined in the eighth layer 18.

FIG. 1B is a top view of the assembled device 10 of FIG. 1A. FIGS. 1C–1D provide expanded views of two portions of the device 10. FIG. 1C shows the sample injection channels 35A–35N with associated enlarged regions 34A–34N that are aligned with the sample inlet ports 28A–28N defined in the first layer 11. For simplicity, the frit 40 has been omitted from FIG. 1C, although FIGS. 1A–1B correctly show the frit 40 placed between the sample vias 36A–36N, 44A–44N upstream of the point where samples are injected onto the separation channels 45A–45N to be filled with packed particulate stationary phase material. FIG. 1D shows the mixing and splitting channel structures that communicate mobile phase solvent to the column-containing channels 45A–45N. During operation of the device 10, a first mobile phase solvent is injected into a first solvent inlet port 22 and flows into channel 64. A second mobile phase solvent is injected into a second solvent inlet port 24 and flows through the channel segment 46 through a slit 52 where it is layered with and joins the first solvent in the channel 64. The two layered solvents mix in the channel 64 and subsequent channel segment 58, whereafter the mixed solvent stream is split into eight portions or substreams by way of transport through a splitter 55 comprising a large forked channel segment 68, two medium forked channel segments 56A, 56B, and four small forked channel segments 66A–66D. The eight solvent mixture substreams are then injected through vias 54A–54N and 48A–48N into the (column-containing) separation channels 45A–45N. For simplicity, the frit 50 disposed between the vias 54A–54N and 48A–48N have been omitted in FIG. 1D, although this frit 50 is properly included in FIGS. 1A–1B.

Preferably, the various layers 11–19 of the device 10 are fabricated from unoriented polypropylene and bonded using an adhesiveless thermal bonding method, such as methods employing platens, as described above. This construction method yields chemically-resistant devices having high bond strength, both desirable attributes for withstanding a column packing process and subsequent operation to provide separation utility.

While separation columns of various lengths may be provided in separation devices according to the present invention such as the device 10, preferably such columns are greater than or equal to about 1 cm in length to provide reasonable separation efficiency. Columns much longer than 1 cm may be fabricated according to methods described herein.

While the device 10 illustrated in FIGS. 1A–1D represents a preferred fluidic device, a wide variety of other fluidic devices may be used. In certain embodiments, fluidic device may include one or more tubes, particularly capillary tubes. For example, capillary tubes may be embedded in one or more channels of a microfluidic device.

As discussed briefly above, particulate material deposited by a slurry packing process (described below) preferably fills the manifold or junction channel 42 and at least a portion of the upstream channel 38. This leaves a "trailing edge" of packing (particulate) material in the channel 38 that is far removed from the injection region (i.e., the mobile phase injection vias 44A–44N adjacent to the frit 40 and the sample injection vias 48A–48N adjacent to the frit 50) where mobile phase and sample are provided to the column-containing channels 45A–45N. In operation, the mobile phase and sample are injected directly onto the columns in channels 45A–45N, well downstream of the trailing edge of particulate material in the channel 38. It is beneficial to avoid sample flow through the trailing edge region of the particulate to promote high-quality separation, since the trailing edge is typically not well-packed. That is, since the quality of separation in chromatography depends heavily on the size of the injection plug, with a small and well-defined plug generally providing better results, it is desirable to avoid injecting a sample into a region that is not uniformly packed with particulate. On-column injection well downstream of the trailing edge of the packing material promotes small and well-defined sample plugs.

In liquid chromatography applications, it is often desirable to alter the makeup of the mobile phase during a particular separation. If multiple separation columns are provided in a single integrated device (such as the device 10) and the makeup of the mobile phase is subject to change over time, then at a common linear distance from the mobile phase inlet it is desirable for mobile phase to have a substantially identical composition from one column to the next. This is achieved with the device 10 due to two factors: (1) volume of the path of each (split) mobile phase solvent substream (shown in FIG. 1D) is substantially the same to each column; and (2) each flow path downstream of the fluidic (mobile phase and sample) inlets is characterized by substantially the same impedance. The first factor, substantially equal substream flow paths, is promoted by design of the composite splitter incorporating elements 58, 68, 56A–56B, and 66A–66D. The second factor, substantial equality of the impedance of each column, is promoted by both design of the fluidic device 10 and the fabrication of multiple column in fluid communication (e.g., having a common outlet) using a slurry packing method disclosed herein. Where multiple columns are in fluid communication with a common outlet, slurry flow within the device 10 is biased toward any low impedance region. The more slurry that flows to a particular region during the packing process, the more particulate is deposited to locally elevate the impedance, thus yielding a self-correcting method for producing substantially equal impedance from one column to the next.

Microfluidic separation devices may include substantially more than eight separation channels, and the number of separation channels need not be an even exponential of two. For example, a microfluidic separation device 610 including twenty-four separation channels 639A–639N is illustrated in FIGS. 6 and 7A–7E. The microfluidic separation device 610 is constructed with twelve device layers 611–622, including multiple stencil layers 614, 615, 617, 618, 620. Each of the twelve device layers 611–622 defines five alignment holes 623–627, which are used in conjunction with external pins (not shown) to aid in aligning the layers during construction or in aligning the device 610 with an external interface such as a clamping apparatus (not shown) during a packing process or during operation of the device 610.

The first through third layers 611–613 define a plurality of sample ports/vias 628A–628N that permit samples to be introduced to a plurality of separation columns 639A–639N (defined in the seventh device layer 617) and a plurality of optical detection windows 630A–630N. Two sample ports 628A–628N and 629A–629N are associated with each separation column 639A–639N to permit injection of precise volumes or "plugs" of sample into each column 639A–639N. Optical detection windows 630A–630N also are defined in the first through eighth and twelfth device layers 611–617, 622. The optical detection windows 630A–630N facilitate optical detection by reducing the amount of material between an optical detector (not shown), such as a conventional UV-Vis detector, and the samples contained in output analysis channels 632A–632N (defined in the tenth device layer 620) downstream of the columns 639A–639N.

The fourth through sixth layers 614–616 define a mobile phase distribution network 640 that includes a mobile phase mixing channel 642, a composite mixing channel 644 (composed of a plurality of mixer segments 646A–646N) and a mobile phase splitter 648 (composed of a plurality of splitter segments 650A–650N). The fourth device layer 614 defines a plurality of sample injection channels 654A–654N. A first frit 652 is disposed between the mobile phase splitter 648 and the sample injection channels 654A–654N. The first frit 652 (and the other frits described below) is preferably constructed from a permeable polypropylene membrane such as, for example, 1-mil thickness Celgard 2500 membrane (55% porosity, 0.209×0.054 micron pore size, Celgard Inc., Charlotte, N.C.). The fifth and sixth device layers 615, 616 define a plurality of sample injection vias 656A–656N and 657A–657N. A second frit 658 is disposed between the sample injection vias 656A–656N in the fifth device layer 615 and the sample injection vias 657A–657N in the sixth device layer 616. The fifth through twelfth device layers 615–622 define the first mobile phase vias 664A–664H, which are in fluidic communication with each other and the mobile phase mixing channel 642.

The fifth and sixth device layers 615, 616 define second mobile phase mixer slits 660, 662, which are in fluidic communication with each other and the mobile phase mixing channel 642. The seventh device layer 617 defines a channel segment 666, which is in fluidic communication with the second mobile phase mixer slits 660, 662 and a plurality of second mobile phase input vias 668A–668D and port 668E defined in the eighth through twelfth device layers 618–622.

The seventh device layer 617 defines the separation channels 639A–639N. The seventh device layer 617 together with the eighth device layer 618 define a slurry distribution network 670 that includes a slurry input channel 672 and a slurry splitter 674 (made up of slurry splitter segments 676A–676N). The eighth through twelfth device layers 618–622 define a plurality of slurry vias 678A–678N, which are in fluidic communication with each other and the slurry input channel 642.

The eighth and ninth device layers 618, 619 define a plurality of separation column output vias 680A–680N in fluid communication with each other and the separation columns 639A–639N. A third frit 682 is interposed between the separation column output vias 680A–680N in the eighth device layer 618 and the separation column output vias 680A–680N in the ninth device layer 619.

The tenth device layer 620 defines a plurality of output analysis channels 632A–632N, each including an optical alignment segment 686A–686N (which is aligned with the optical detection windows 630A–630N defined in the first through eighth and twelfth device layers 611–617, 622. Effluent vias 689A–689N, 688A–688N are defined in the eleventh and twelfth device layers 621, 622 and are in fluid communication with each other and the output analysis channels 632A–632N. Fourth and fifth frits 690, 692 are interposed between the effluent vias 689A–689N in the eleventh device layer 621 and the effluent vias 688A–688N in the twelfth device layer 622.

In operation, the columns 639A–639N of the device 610 are packed with the desired stationary phase material, typically silica-based particulate such as C-18 silica particles. A slurry of a solvent (such as acetonitrile) and particulate is injected through the slurry vias 678A–678N into the slurry input channel 672 and the slurry splitter 674, whereupon the slurry is distributed to each of the columns 639A–639N. The second and third frits 658, 682 prevent the slurry from exiting the columns 639A–639N through either the separation column output vias 680A–680N or the sample injection vias 656A–656N. Once the columns 639A–639N are packed, the slurry input channel 672 may be sealed to prevent unpacking therethrough. Alternatively, solvent may be injected through the slurry input channel 672 during operation of the separation device, thus allowing the fluidic pressure of the solvent to maintain the desired packing density.

To perform a chromatographic separation using the device 610, the packed device is placed in a chromatography instrument having a clamshell-type gasketed interface, such as described in copending U.S. patent application Ser. No. 60/422,901 filed on Oct. 31, 2002, which application is hereby incorporated by reference. One or more solvents are provided to the device 610 through the first and second solvent input ports 664H, 668E. If two solvents are used (for example, to perform a gradient separation) the solvents are combined as the second solvent enters the solvent mixing channel 642 through the second mobile phase mixer slits 660, 662. The convoluted channel formed by channel segments 646A–646N serves to provide sufficient channel length to permit mixing downstream of the overlap between slit 662 and the mixing channel 642 (enhanced by the plurality of directional changes experienced by the mobile phase). After the mixing, the mobile phase enters the mobile phase splitter 648, where it is evenly distributed to each of the columns 639A–639N and flows out of the device through the effluent vias 689A–689N and outlet ports 688A–688N.

Once the device 610 is thoroughly wetted with mobile phase, the flow of mobile phase is suspended and samples are injected into the sample input ports 628A–628N. Once the samples are input, the sample input ports 628A–628N are sealed and the flow of mobile phase is resumed, carrying the samples through the columns 639A–639N thereby performing the desired separation. Analytical instruments (not shown) may observe the results of the separation through the optical detection windows 630A–630N. Alternatively, or additionally, the effluent may be collected from the effluent vias 688A–688N for additional analysis.

Preferably, the various layers 611–622 of the device 610 are fabricated from unoriented polypropylene and bonded using an adhesiveless thermal bonding method utilizing platens, as described above. This construction method yields chemically-resistant devices having high bond strength, both desirable attributes for withstanding a column packing process and subsequent operation to provide separation utility.

Clamping Apparatus

Microfluidic devices such as the devices 10 or 610 may be placed within a clamping apparatus to assist with column packing. A first representative clamping apparatus is shown in FIGS. 2A–2F. The clamping apparatus includes a first (upper) plate 100 and a second (lower) plate 130. As shown in FIG. 2F, the two plates 100, 130 may be sandwiched around a microfluidic device (such as the device 10 described previously) and fastened with bolts 140. The upper plate 110 has through-holes 102A, 102B disposed along the sides of the plate 110 and designed to mate with corresponding (tapped) holes 102B, 104B in the lower plate 130 for accepting the bolts 140. To aid in aligning a microfluidic device between the two plates 100, 130, multiple raised pins 108 may be provided in the second plate 130 to penetrate apertures (e.g., holes 20, 21 in device 10) in a microfluidic device and mate with recesses 106 in the first plate 106. When the two plates 100, 130 sandwich a microfluidic device, the inner surfaces 124, 134 of the plates abut the device and face one another, with the outer surfaces 122, 132 of the plates 100, 130 facing outward.

Several features are provided to aid in interfacing the clamping apparatus with a microfluidic device to promote column packing. The first 110 defines a cutout region 110 that provides an unobstructed path for slurry to enter an inlet port such as the fluidic port 26 shown in FIG. 2E. The first plate 100 defines a recess 112 into which a gasket 113 is inserted; this gasket 113 mates with the sample inlet ports 28 during the packing step to prevent the entry of slurry into the ports 28. Further defined in the first plate is a tapped recess 117 along one edge for accepting a high-pressure fitting (not shown) through which solvent separated from the packing slurry may exit the microfluidic device. The recess 117 includes an aperture or fluid passage 118 that connects to another fluidic passage or recess 116 that penetrates the inner surface 124 of the first plate 100. The fluidic passage 116 penetrates a surface 115 that is at approximately the same level as the bulk of the inner surface 124, but is raised in comparison to a surrounding annular recess 114 that is designed to hold an annular gasket (not shown). As shown in FIG. 2E, a fluidic port 30 of a microfluidic device 10 is designed to exhaust fluid (solvent) from the device 10 during the packing process into the fluidic passage 116 (and onward to passage 116 and an external fluid-conveying fitting leading to a conduit exiting the apparatus), such that the surface of the device 10 immediately surrounding the fluidic port 30 sealingly engages the gasket contained in the annular recess 114 to avoid unintended fluid leakage. In this manner, the clamping apparatus including upper and lower plates 100, 130 facilitates the unobstructed entry of slurry into a microfluidic device, and provides for leak-free conduction of solvent separated from that slurry away from the microfluidic device.

Another representative clamping apparatus 299 is shown in FIGS. 4A–4B. The clamping apparatus includes a first plate 300 and a second plate 330. The clamping apparatus 299 is adapted to pack three microfluidic devices (such as the device 10 described previously) with stationary phase material; however, it will be readily apparent to one skilled in the art that clamping apparatuses for packing any desired number of devices may be provided by increasing or decreasing the size of the clamping device 299 and replicating the clamping device 299.

As shown in FIG. 4A, the two plates 300, 330 may be sandwiched around a microfluidic device 30A and fastened with bolts 340 and nuts 341. The first plate 300 has through-holes 302A, 304A disposed along the sides of the first plate 300 and designed to mate with corresponding holes 302B, 304B in the second plate 330 for accepting the bolts 340. To aid in aligning a microfluidic device 10A between the two plates 300, 330, multiple raised pins 308 may be provided in the first plate 300 to penetrate apertures (e.g., holes 20, 21 in device 10) in a microfluidic device and mate with recesses 306 in the second plate 330.

As before, several features are provided to aid in interfacing the clamping apparatus 299 with a microfluidic device 10 to promote column packing. The second plate 330 defines a slurry port 310 that provides an unobstructed path for slurry to enter an inlet port of the device 10. The first plate 300 defines a recess 312 into which a gasket 313 is inserted; this gasket 313 mates with the sample inlet port 328 of the microfluidic device 10 during packing to prevent the release of pressure during the packing process. Similarly, the first plate 300 defines a recess 314 into which a gasket 315 is inserted; this gasket 315 mates with the solvent inlet ports 22, 24 during the packing step to prevent the release of pressure during the packing process. As shown in FIGS. 4B, 5A, these features may be repeated to accommodate three (or even more) microfluidic devices 10A–10N (numbering for the features associated with the additional microfluidic devices 10 that may be secured by the clamping mechanism 299 are omitted for simplicity).

Slurry packing systems and methods

In a preferred embodiment, at least one fluidic device is slurry-packed using a pressure vessel. A system 200 that may be used to accomplish this result is shown in FIG. 3. While only a single device 202 is illustrated as being contained within the vessel 210, multiple devices may be packed simultaneously within a pressure vessel according to methods disclosed herein. A pressure vessel 210 contains a slurry bath 208, with a fluidic device 202 placed therein such that a slurry inlet port 206 in the device 206 is fully immersed in the bath 208. The fluidic device 202 includes a fluidic connection 204 to provide a substantially leak-free connection to an external solvent collection device 216 that is preferably maintained at or below atmospheric pressure. When the pressure vessel is pressurized (by way of a pressure source 226, pressure regulator 228, and associated valving 230 and conduits, a pressure differential is created across the fluidic device 202 (by virtue of fluid connections to both pressure vessel 210 and the solvent collection device 216) that motivates slurry to flow from the slurry bath 208 into the device 202. Within the device 202, at least one frit (not shown) is preferably provided to retain particulate material from the slurry yet permit solvent to pass through to the solvent collector 216.

Preferably, operation of the system 200 is automated at least in part with controller 240. While various controller types may be used, the controller 240 is preferably microprocessor-based and is capable of executing software including a sequence of user-defined instructions. The controller 240 preferably interfaces with substantially all of the devices controlling inputs to and outputs from the pressure vessel 210. For example, the controller 240 may control the flow of slurry from a slurry supply reservoir or device 218 to the vessel 210 by operating a slurry supply valve 220. Preferably, slurry to be supplied to the vessel 210 is supplied under pressure at least above atmospheric pressure, utilizing means such as a pump or pressure supply (not shown) associated with the slurry supply device 218 to motivate slurry flow into the vessel 210. In a similar fashion, the controller 240 may control the flow of slurry from the vessel 210 to a slurry collection reservoir or device 222 by controlling a slurry exhaust valve 224. The slurry bath 208 may be stirred (preferably continuously) by way of a stirbar 212 located within the vessel 210, with motion of the stirbar 212 being motivated by a magnetic stirplate 214 having a connection to the controller 240.

As for pressurization of the vessel 210, the controller 240 may interface with a regulator 228 and valve 230 that control the supply of a pressurized gas (such as compressed nitrogen, for example) from a pressure source 226 to the vessel 210. The controller 240 preferably controls a throttling valve 232 having a connection to a vent 234 to permit controlled ventilation of the pressurized gas from the vessel 210 toward the conclusion of a packing process.

Applicants have successfully packed microfluidic devices according to the design of the device 10 disclosed herein with a simplified system (compared to the system 200) lacking automatic control. A ZipperClave® Model ZC0200SS02 pressure vessel (Autoclave Engineers, Erie, Pa.) having a detachable lid was modified to accept several fluid connections through the lid: a gas conduit, a slurry outlet, and a solvent outlet. The gas conduit was capable of providing regulated pressurized nitrogen from an external pressurized nitrogen canister, and also slowly exhausting pressurized nitrogen from the pressure vessel through a manually-operated needle valve. The slurry outlet included a long metal tube to extract slurry from near the bottom of the vessel; this outlet was connected to a manually operated external valve that could be opened to permit pressurized slurry to flow from the vessel. The solvent outlet was connected to a clamping apparatus according to that shown in FIGS. 2A–2F surrounding a microfluidic device 10 (illustrated in FIGS. 1A–1B), with a leak-free connection provided between the solvent outlet 30 and an external solvent collector provided by way of conventional threaded tubing and fittings. More specifically, the clamping apparatus (including first and second plates 100, 130) and clamped microfluidic device 10 were suspended in the vessel by way of the solvent outlet conduit such that the slurry inlet port 26 was disposed toward the bottom of the vessel and the solvent port 30 was disposed toward the vessel lid.

In the simplified system, the vessel was placed atop a magnetic stirplate (Corning model PC-353 stirrer) and a magnetic stirbar capable of being set in motion by the stirplate was placed into the vessel. A slurry was prepared by mixing 1.00 grams of Pinnacle II™ C-18 (silica) powder, 5 micron, catalog no. 551071 (Restek, Bellefonte, Pa.) with 500 mL of acetonitrile (MeCN) liquid. A portion of this slurry was manually added to the vessel to a sufficient level to submerge the slurry inlet port 26 of the microfluidic device 10 upon its addition to the vessel. Significantly, use of the rotating stirbar in the slurry ensures that slurry entering the microfluidic device is fully mixed up to the slurry inlet port, thus reducing the possibility of clogging at the inlet port. With fully mixed slurry entering the microfluidic device, it is anticipated that more concentrated slurries (i.e., slurries having relatively more particulate matter and relatively less solvent) can be used than are commonly employed in conventional slurry packing methods, thus permitting packing to be accomplished more quickly. Preferably, particles useful for packing fluidic devices disclosed herein and according to packing methods disclosed herein comprise silicon, zirconium, or polymeric materials. The use of frits renders unnecessary sintering processes, which are typically used to retain particles in a separation channel. The packed particles preferably comprise at least one surface functional group to permit the resulting devices to be used with high performance liquid chromatography methods. Examples of desirable surface functional groups include alkyl, cyano, amino, nitro, hydroxy, phenyl, phenylhexyl, and sulfonic acid.

With the vessel sealed, pressurized nitrogen was added to the vessel to motivate slurry to enter the microfluidic device 10 and flow toward the (low pressure) solvent outlet. The device 10 included a frit 51 that retained particulate within the device 10 but allowed solvent to pass therethrough to exit the device 10 through the fluidic port 30. Pressurized nitrogen was added to the vessel according to a six-step pressure ramp, with each step lasting about twenty minutes. The pressure was maintained at 200 psi (1379 kPa) for 20 minutes, and then ramped upward to 400, 600, 800, 1000, and 1200 psi (2758, 4137, 5516, 6895, and 8274 kPa) for the remaining pressure ramp steps. During application of the pressure ramp, solvent separated from the slurry flowed from the device 10 through fluidic port 30, then exited the vessel through the clamping apparatus and solvent outlet. The solvent was collected in a container having graduated markings. Monitoring progress of the column packing is a straightforward exercise if both the slurry makeup (proportion of particulate/solvent) and the volume of the fluidic structure to be packed with particulate are known. In this regard, it is helpful to monitor the accumulated solvent volume that has exited the device, the flow rate of solvent exiting the device, or both. Notably, a sudden drop in solvent flow rate exiting the device typically signals successful particulate packing of a specific fluidic volume using slurry packing methods disclosed herein. However, when the desired column volume is particularly small, then it may be more practical to monitor accumulated volume than flow rate. Feedback control of the pressure application (ramp) step based upon accumulated solvent volume or flow rate of solvent exiting a fluidic device is contemplated, as discussed in connection with FIG. 3.

Following application of the six-step pressure ramp, which lasted about two hours in total, a valve between the nitrogen supply pressure regulator and the vessel was closed. Then a slurry outlet valve was opened to permit the removal of (pressurized) slurry from near the bottom of the vessel. Once the slurry had been drained to a level well below the slurry inlet 26 of the device 10, taking care not to drop the pressure too quickly in the vessel, the slurry outlet valve was closed. Thereafter the needle valve was opened to allow the vessel to slowly depressurize to atmospheric pressure. This slow venting step has been accomplished in approximately 30–60 minutes. It is believed that slow venting assist in purging solvent and dissolved gas from the packed column(s), thus helping to prevent "blowback" of packing that would reduce its efficacy (i.e., "unpack" the particulate material). With the pressure fully vented from the vessel, the vessel was opened and the clamped device 10 was removed.

After completion of all packing steps, the slurry inlet port 26 may be sealed. One sealing method that has been successfully employed uses epoxy by first making a two-part epoxy mixture and then injecting the mixture into the slurry inlet port 26 until it reaches the trailing edge of particulate matter contained in the channel 38. Applicants have successfully used Devcon S-209 "5 minute fast drying epoxy" (ITW Devcon, Des Plaines, Ill.) for this task, although other equivalent sealing methods could be used. Sealing the packing material provides at least two advantages. First, it prevents the columns from un-packing. Second, sealing the slurry inlet port 26 and channel 38 limits the amount of flow of mobile phase or sample in an undesired direction (i.e., away from the outlet port 30).

Following initial slurry packing of a fluidic device but before a slurry inlet port is sealed, an optional further step to ensure tight packing of the columns may be employed. A pressurized fluid may be introduced into the slurry inlet port (e.g. port 26) and flowed through the column-containing channels (e.g., channels 45). Mobile phase solvent such as acetonitrile may be used for this purpose.

An alternative packing method and apparatus is capable of packing fluidic devices without the use of elevated pressures and pressure vessels. Instead, a pressure differential sufficient to motivate slurry to flow into a fluidic device (such as, for example, the device 10 described previously) may be generated by connecting a fluidic port 30 of such a device to a vacuum source such as a vacuum pump. If the slurry inlet port 26 of such a device 10 is submerged in an slurry bath at atmospheric pressure, then a pressure differential of nearly one atmosphere (101 kPa) can be developed across the device with the outlet connected to vacuum. Compared to the packing methods employing pressure vessels and highly elevated pressures, atmospheric pressure packing is anticipated to take a much longer time to yield packed columns with satisfactory results. On the other hand, atmospheric packing methods avoid volume limitations along with capital and operating expenses associated with pressure vessels. As a result, it is contemplated that an extremely large number of fluidic devices may be packed simultaneously in using an open, atmospheric trough containing a bath of stirred slurry. Each fluidic device may be connected to one or more vacuum sources by way of individual fluid conduits or a common vacuum manifold.

In yet another alternative packing method, pressurized slurry may be supplied to one or more fluidic devices having a solvent outlet vented to a low-pressure region such as atmosphere or vacuum. Preferably such a packing method is applied to one or more microfluidic devices having multiple columns in fluid communication at a common solvent outlet. A slurry supply manifold may be employed. In such an embodiment, however, where pressurized slurry is routed via fluid conduit to a slurry inlet (rather than using a slurry bath), it is difficult to ensure that completely stirred slurry is provided to the devices.

In another embodiment, a rotatable pressurized vessel may be used. For example, referring to FIGS. 5A–5C, one embodiment of a multicolumn packing system 500 according to the present invention utilizes ultrasonic energy and a rotatable pressurized vessel 502 to deliver slurry to one or more microfluidic devices 10A–10N. The system 500 comprises a sampling vessel 502, a pressure source 504, a rotary actuator 506, a plurality of slurry delivery conduits 508A–508N, and an ultrasonic bath 510.

The sampling vessel 502 may be any suitable cylindrical vessel capable of containing the pressures required for the packing process. In the embodiment illustrated in FIGS. 5A–5C, the sampling vessel 502 is a 8" long×2" outside diameter, 0.3 liter stainless steel vessel with hemispherical ends (SS-DOT sample cylinder, Hoke Inc., Clifton, N.J.). The sampling vessel 502 is suspended in a horizontal position and rotatably (and preferably, removably) mounted to a frame (not shown) using brass bushings suspended in fixed collars (or, alternatively, bearings) at either end or any other suitable rotatable mounting mechanism. A fluidic connection 516 to the sampling vessel 502 is permitted through at least one end bushing. The sampling vessel 502 and associated slurry delivery conduits 508A–508N (leading to one or more microfluidic devices 10A–10N) may be rotated through a range of about ninety degrees (as shown in FIGS. 5B–5C), preferably by way of actuating means 506, such as a rotary actuator, a linear actuator with an appropriate linkage, or another suitable actuator. Preferably, a programmable controller 507 is coupled to the actuating means 506 to control periodic rotation of the sampling vessel 502.

A solvent 512 (such as acetonitrile) and particulate 518 (such as C-18 silica particles) are contained in the sampling vessel 502. Because the sampling vessel 502 is suspended horizontally, the contents are gravitationally stratified along the length of the sampling vessel 502. Referring to FIG. 5B, when the sampling vessel 512 is disposed in an "un-rotated" (0 degrees) position with the slurry delivery conduits 508A–508N positioned horizontally, the level of the particulate material 518 within the sampling vessel 502 is below the level of the slurry delivery conduits 508A–508N, so only solvent 512 is supplied through the slurry delivery conduits 508A–508N to the microfluidic device(s) disposed and fluidically coupled below (as shown in FIG. 5A). Referring to FIG. 5C, when the sampling vessel 502 is disposed in a rotated (e.g., 90 degrees) position, however, the slurry delivery conduits 508A–508N are positioned at the bottom of the sampling vessel 502, below the level of the particulate 518 within the sampling vessel 502, so particulate 518 (along with solvent 512) is supplied to the microfluidic device(s) below (not shown, see FIG. 5A). Referring again to FIG. 5A, a pressure source 504, such as a Shimadzu LC-10AT pump (Shimadzu Scientific Instruments, Inc., Columbia, Md.) or other suitable pressure source, aided by gravity, provides the flow velocity to carry the particulate 518 from the sampling vessel 502 into the slurry delivery conduits 508A–508N. Preferably, a tube oscillator 520 (e.g., each comprising a motor, such as a small 3600 RPM motor, having an offset cam) is affixed to each slurry delivery conduit 508A–508N to vibrate the particulate 518 within each slurry delivery conduit 508A–508N to break up any possible particle clumps, thus reducing the chance of blockage further downstream. Preferably, the slurry delivery conduits 508A–508N include at least portions that are flexible to accommodate rotation of the sampling vessel 502 through at least about a ninety degree range.

Each microfluidic device 10A–10N to be packed includes porous frits 40, 50, 51 adapted to retain the particulate material 518 within the microfluidic device 10A–10N (see FIG. 1A). To this end, the pore size of the frit material should be smaller than the size of the particulate 518 to be packed within the microfluidic devices 10A–10N. While various frit materials may be used, one preferred frit material is one mil (25 micron) thickness Celgard 2500 membrane (55% porosity, 0.209×0.054 micron pore size, Celgard Inc., Charlotte, N.C.). As solvent 512 and particulate material 518 are provided to each microfluidic device 10A–10N, the solvent 512 preferably flows through the frits 40, 50, 51 and exits the microfluidic devices 10A–10N, while the particulate material is retained within each microfluidic device 10A–10N by the frits 40, 50, 51. Upon entering each microfluidic device 10A–10N, the particulate material 518 settles down to the bottom of the columns 45 to be packed. Having each microfluidic device 10A–10N at least partially immersed in an ultrasonic bath 510 helps to break up any potential particulate blockages within each microfluidic device 10A–10N and helps to facilitate dense packing. The process of rotating the sampling vessel 502 is preferably repeated approximately ten to fifteen times, with five to ten second dwell times for supplying particles to the slurry delivery conduits 508A–508N, and sixty to ninety second dwell times for supplying only solvent to the slurry delivery conduits 508A–508N.

In a preferred embodiment, multiple microfluidic devices 10A–10N are packed simultaneously by way of multiple slurry delivery conduits 508A–508N emanating from the sampling vessel. FIGS. 4A–4B, 5A–5C illustrate a system and apparatus for the simultaneous packing of three microfluidic devices 10A–10N, but scaling up to simultaneously pack a much greater number of microfluidic devices 10A–10N is a relatively simple matter of providing a solvent vessel 502 of appropriate dimensions, providing an appropriate number of slurry delivery conduits 508A–508N from the sampling vessel, providing a clamping mechanism 99 adapted to secure the desired number of microfluidic devices 10A–10N, ensuring appropriate solvent flow (e.g., by larger and/or additional pumps if necessary), and providing an ultrasonic bath 510 of appropriate size/volume.

Referring to FIG. 5A, three microfluidic devices 10A–10N may be packed using the above-described components. First, approximately 80 grams of particulate 518 (in this case, Microsorb C-18 silica) is supplied to the sampling vessel 502 at one end of the cylinder—preferably the end to which the pressure source 504 connects to prevent particles from entering the pump inlet tubing 505. The addition of particulate 518 to the sampling vessel 502 is aided by wetting the particles first with solvent 512 (in this case, 100% tech grade acetonitrile). After all of the particulate 518 is added to the sampling vessel 502, the sampling vessel 502 is filled with solvent 512 (again, 100% tech grade acetonitrile). It is believed that minimizing the presence of air within the sampling vessel 502 is beneficial to avoid an unduly slow pressure ramp when the pressure source 504 is activated during the packing procedure—since the pressure source 504 will compress any air within the sampling vessel 502. Once the sampling vessel 502 is filled with particulate 518 and solvent 512, the pressure source 504 (an HPLC pump) is activated to fill the inlet tube 505 with solvent 518 so as to eliminate air in the inlet tube 505. When the inlet tube 505 is filled, the inlet tube 505 is attached to the vessel with an appropriate leak-free connection (in this case, a stainless steel NPT to ⅛" OD tubing connection). It is recommended to minimize the presence of air in the vessel and associated tubing.

The sampling vessel 502 is then coupled to an actuator 506 capable of rotating the sampling vessel 502 through a ninety degree rotation range and capable of dwelling at each of the zero degree and ninety degree positions for user-defined intervals. As the sampling vessel 502 is coupled to the actuator 506, care should be taken to prevent particulate material from falling into the slurry delivery conduits 508A–508N, since such an event could cause the slurry delivery conduits 508A–508N connections to become clogged during packing. The slurry delivery conduits 508A–508N comprise first tubes emanating from the vessel 502, the first tubes being approximately twelve inch long sections of ⅛" OD×1/16" ID flexible tubing able to withstand at least 1000 psi (6.9 MPa). Each of these tube sections are connected to smaller ID tube sections (each approximately 6 inches long with 1/16" OD×0.005" ID) with appropriate connectors, such as Upchurch superflangless connectors and union connectors. Both ends of the smaller tubing each have another connector (e.g., Upchurch superflangless connectors), one of which connected to the Upchurch union connector and the other of which connected directly to the packing inlet of the clamping mechanism 99, to deliver slurry to the microfluidic devices 10A–10N suspended therein.

Each microfluidic device 10A–10N is disposed at least partially within the ultrasonic water bath 510 to permit direct contact between each device 10A–10N and the sonication fluid (e.g. water). An ultrasonic bath 510 is merely one example of a mechanism for vibrating, agitating, or otherwise adding energy to each device 10A–10N to promote denser packing. A portion of each device 10A–10N is suspended approximately 0.25 inches deep in the ultrasonic bath 510. One example of such an ultrasonic bath 510 is a Branson Model 8500 (Branson Ultrasonics Corp. Danbury Conn.), which is maintained during the packing procedure at a 50% power setting with the frequency/transducer sweep turned on.

With the sampling vessel 502 filled and appropriately connected to the microfluidic devices 10A–10N, the solvent (e.g., HPLC) pump 504 is activated to initiate constant flow rate of one ml/min to verify that the pressure ramping starts within about five seconds. If the pressure ramp does not start within this interval, this typically indicates the presence of an air pocket in the vessel or tubing that can detrimentally affect packing efficiency. When the system is determined to be substantially free of air pockets, packing is initiated. The ultrasonic bath 510 and tube oscillators 520A–520N are activated, and the packing sequence (including multiple steps of alternating the supply of particulate 518 and the supply of solvent 512 to the microfluidic devices 10A–10N by rotating the sampling vessel 502) is initiated. Table 1 indicates the dumping times and dwell times according to a preferred embodiment.

TABLE 1

Dumping and dwell times for packing of microfluidic devices.

| Step | Rotation Angle (degrees) | Dwell Time (secs) |
|---|---|---|
| 1 | 90 | 5 |
| 2 | 0 | 30 |
| 3 | 90 | 5 |
| 4 | 0 | 30 |
| 5 | 90 | 5 |
| 6 | 0 | 30 |
| 7 | 90 | 5 |
| 8 | 0 | 30 |
| 9 | 90 | 5 |
| 10 | 0 | 30 |
| 11 | 90 | 5 |
| 12 | 0 | 30 |
| 13 | 90 | 5 |
| 14 | 0 | 30 |
| 15 | 90 | 5 |
| 16 | 0 | 30 |
| 17 | 90 | 5 |
| 18 | 0 | 30 |
| 19 | 90 | 5 |
| 20 | 0 | 30 |
| 21 | 90 | 5 |
| 22 | 0 | 30 |
| 23 | 90 | 5 |
| 24 | 0 | 30 |
| 25 | 90 | 5 |
| 26 | 0 | 300 |

This combination of process steps for purposes of illustration; other combinations of dump time and dwell time may be used.

To prevent rupture of the microfluidic devices 10A–10N and provide repeatably dense column packing, a pressure sensor (not shown) in sensory communication with the solvent supply system is preferably provided and connected to a controller 507 to maintain the supply pressure within a desired range. Preferably, the controller 507 receives user-defined settings for minimum and maximum pressure and controls activation of the pressure source 504 to maintain the solvent supply pressure within a desired range (e.g., between 270–300 psi/1860–2070 kPa). If the pressure source 504 is set to supply a constant flow rate, it may be periodically activated and deactivated to maintain pressure within the desired range. Alternatively, a pressure regulator (not shown) may be supplied between the pressure source 504 and the sampling vessel 502 to regulate the supply pressure. Also, sudden and/or large changes in system pressure may indicate a problem with the packing process, such as clogging within or burst of one of the microfluidic devices 10A–10N. Individual pressure sensors (not shown) may monitor the pressure within each of the slurry delivery conduits 508A–508N to allow the determination of which microfluidic device 10A–10N is the source of the pressure change. Valves (not shown) also may be included in each of the slurry delivery conduits 508A–508N to allow selective closure of the slurry delivery conduits 508A–508N to remove the problematic microfluidic device 10A–10N from the system. The controller 507 may then adjust the pressure and flow rates to reflect the change in the number of microfluidic device 10A–10N being packed.

Upon completion of the last step (e.g., 26th step), the ultrasonic bath 510 and the tube oscillators 520A–520N are deactivated, and the (packed) microfluidic devices 10A–10N are removed from the ultrasonic water bath 510.

In another embodiment, a relatively dilute or "thin" slurry (i.e., having a high concentration of solvent and a low concentration of particulate matter) may be used. It is believed that thin slurries help promote more densely packed separation channels by providing a slow buildup of particles within the columns. It is also believed that thin slurries help avoid problems with particulate clogging the packing components. One difficulty, however, in trying to utilize thin slurries of particulate matter not soluble in the accompanying solvent is that the particulate tends to settle downward due to the force of gravity. As will be recognized by one skilled in the art, there exist numerous ways to agitate or otherwise add energy to a solvent/particulate mixture to distribute particulate within the solvent. Several examples of systems for providing thin slurries to separation devices to pack separation channels follow.

Figure 8:
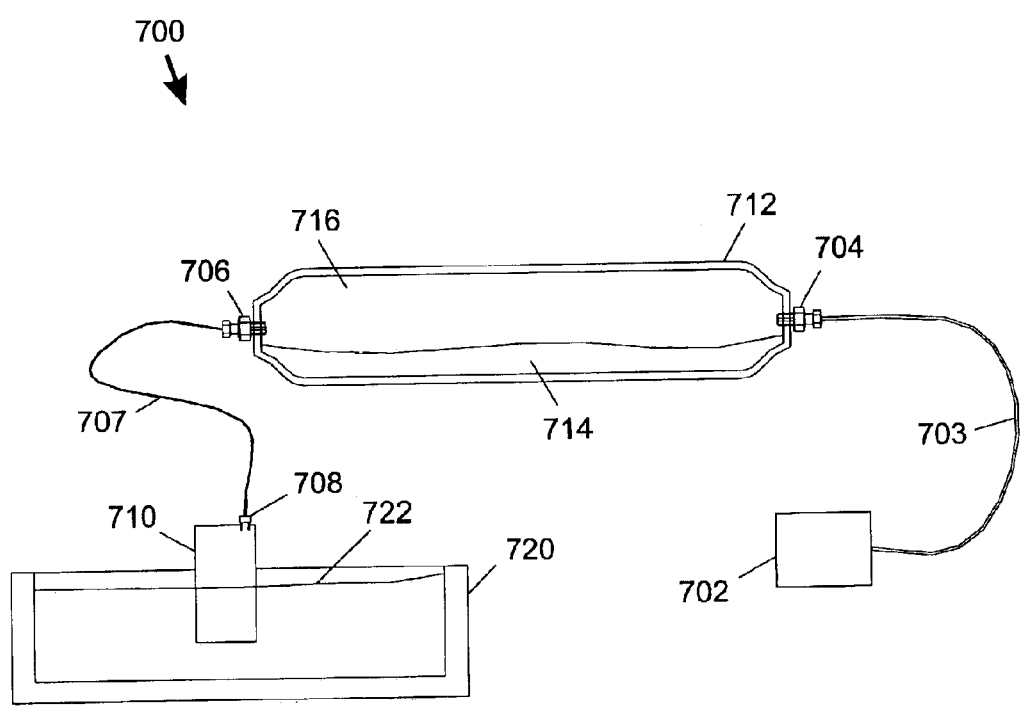
FIG. 8 is a schematic illustration of a system utilizing a horizontally disposed cylinder for packing at least one separation column.

In one embodiment, particulate is agitated by manual action to maintain a sufficient amount of particulate entrained in a solvent. For example, referring to FIG. 8, a column packing system 700 includes a pressure vessel 712 containing particulate material 714 and (liquid) solvent 716. (While FIG. 8 illustrates a sharp line between the particulate material 714 and the solvent 716, during operation of the system 700 the bulk of the particulate material 714 is preferably substantially dispersed within the solvent volume). A solvent pump 702 supplies pressurized solvent from a solvent reservoir (not shown) to the pressure vessel 712 by way of tubing 703 and a solvent inlet 704 having a threaded fitting. Slurry is supplied from the pressure vessel 712 to at least one fluidic device 710 through a slurry outlet 706, tubing 707, and a fitting 708 preferably engaged to a clamping apparatus (such as described previously herein) providing a pressure-tight connection to the at least one fluidic device 710. Preferably, valves (not shown) are provided in fluid communication with the tubing 703, 707. The fluidic device 710 is preferably at least partially immersed in a liquid 722 contained by a (ultrasonic) sonicator bath 720. During operation of the system 700, the vessel 712 is preferably shaken and/or periodically impacted (such as with a hammer) to maintain a sufficient amount of particulate distributed within the solvent.

In one packing method utilizing the system 700, 14 grams of Luna 10 micron C-18 chromatographic stationary phase particulate material (Phenomenex Inc., Torrance, Calif.)

were added to approximately 100 ml of HPLC grade isopropyl alcohol ("IPA") (Fisher Scientific, Pittsburgh, Pa.) in a flask and the combination was sonicated in a water bath in an open sonicator (Branson Model 8500, Branson Ultrasonics Corp., Danbury, Conn.) for approximately 5 minutes. The resulting wetted slurry was supplied through a funnel to a 0.3 liter stainless steel cylindrical vessel 712 with hemispherical ends (SS-DOT sample cylinder, Hoke Inc., Clifton, N.J.). The slurry-containing cylinder 712 was then filled until overflowing with additional HPLC grade IPA 716 to displace air from the cylinder 712. A Shimadzu LC-10AT HPLC pump (Shimadzu Scientific Instruments, Inc., Columbia, Md.) was connected via 1/16" OD flexible polytetrafluoroethylene tubing 703 to one end of the cylinder 712, and a packing manifold (similar to the apparatus 299 shown in FIGS. 4A–4B) clamped around a microfluidic device 710 (containing twenty-four separation channel according to the design of the device 610 illustrated in FIGS. 6, 7A–7E) was connected to the other end of the cylinder 712 using the tubing 707 of the same type as the other tubing 703. The packing manifold and a portion of the microfluidic device were immersed in a water-filled bath 722 of an open sonicator 720 (Fisher model FS30, Fisher Scientific, Pittsburgh, Pa.). The downstream end of the microfluidic device 710 was exposed to air. The suction side of the HPLC pump 702 was connected to a reservoir (not shown) of HPLC grade IPA. Upon connecting the components, the cylindrical vessel 712 was oriented in a horizontal position, the sonicator 720 was activated, and the HPLC pump 702 was activated and set to a constant pressure of 150 psi (1030 kPa) to supply slurry to the microfluidic device 710. Approximately once every five minutes, the cylindrical vessel 712 was manually rotated into a vertical position, manually impacted roughly 10 times with a 1-lb (0.45 kg) dead blow hammer, then rotated 180 degrees into the opposing vertical position and manually impacted roughly another 10 times with the hammer, and then returned to a horizontal position. It is believed that the preceding rotation and impacting steps functioned to loosen particles 714 that had settled along the lower portion of the cylinder wall and distribute them back into the liquid 716. The microfluidic device 710 was partially filled under these conditions until about 1 inch of packing material was present in the least packed separation channel of the device 710. After that, the pressure of the pump 712 was increased to 350 psi (2410 kPa), still continuing the periodic rotation and impacting steps, until substantially all of the microfluidic channels upstream of the frits were filled with particulate stationary phase material. The microfluidic device 710 and manifold were then removed from the sonicator bath 720, a valve (not shown) disposed between the microfluidic device 710 and the cylinder 712 was closed, and the pump 702 was de-activated. The microfluidic device 710 was left within the manifold for approximately five minutes to permit pressure to escape through the downstream end of the microfluidic device 710 before disengaging the microfluidic device 710 from the manifold.

The resulting packed device 710 had column lengths of about 8 cm. When Luna C18 15 micron chromatographic stationary phase particulate material (Phenomenex Inc., Torrance, Calif.) was used to pack the columns, and the device 710 was operated to perform high performance liquid chromatography at greater than 450 psi (3100 kPa) and a mobile phase flow rate of about 15 microliters per minute per column, separation efficiencies of about 400 theoretical plates (ASTM) were obtained for each column, which translates into a per unit length efficiency of about 5,400 plates per meter. Even greater efficiencies can be obtained using smaller packing material, and by manipulating the mobile phase flow rate.

Another column packing system 730 is illustrated in FIG. 9. This system 730 is similar to the system 700 illustrated in FIG. 8, but includes a mechanical stirring mechanism. The system 730 includes a pressure vessel 742 containing particulate material 744 and (liquid) solvent 746. A solvent pump 732 supplies pressurized solvent from a solvent reservoir (not shown) to the pressure vessel 742 by way of tubing 733 and a solvent inlet 734 having a threaded fitting. An impeller 748 within the vessel 742 is coupled to an external motor 743 by way of a shaft 747. A pressure-tight fitting 738 permits the impeller to be operated while the pressure vessel 742 is pressurized. Slurry is supplied from the pressure vessel 742 to at least one fluidic device 740 through a slurry outlet 736, tubing 737, and a fitting 738 preferably engaged to a clamping apparatus (such as described previously herein) providing a pressure-tight connection to the at least one fluidic device 740. Preferably, valves (not shown) are provided in fluid communication with the tubing 733, 737. The fluidic device 740 is preferably at least partially immersed in a liquid 752 contained by a (ultrasonic) sonicator bath 750. During operation of the system 730, the impeller 748 is rotated by the motor 743 and shaft 747 to maintain a sufficient amount of particulate 744 distributed within the solvent 746. A diluted mixture of entrained particles is supplied to the microfluidic device(s) 740 to permit a slow, dense buildup of particles within the separation channels contained in the device(s) 740.

A further column packing system 760 is illustrated in FIG. 10. This system 760 is similar to systems described previously herein, but rather than relying upon agitation of particulate within a pressure vessel, the system 760 permits slow addition of particulate to a flow of solvent. The system 760 includes a reservoir 772 containing particulate material 774 and (preferably) solvent 746 to displace air from the reservoir. The reservoir 772 has a cap 771 on one end. The bottom of the reservoir 772 includes a particulate outlet 764 that connects to a tee 778. A solvent pump 762 supplies pressurized solvent from a solvent reservoir (not shown) through the tee 778. Particles from the reservoir 772 slowly "spill" out of the vessel into the solvent stream as it passes through the tee 778. Particulate 774 can be forced out of the reservoir 772 by reducing the pressure in the solvent stream (e.g., by deactivating and quickly reactivating the pump 762, or opening a valve (not shown) to release some pressure, etc.). The resulting mixture formed in the tee 778 flows through tubing 767 and a fitting 768 preferably engaged to a clamping apparatus (such as described previously herein) providing a pressure-tight connection to at least one fluidic device 770. The flow rate of the solvent supplied by the pump 762 may be adjusted, and/or the size of the orifice between the reservoir 772 and the tee 778 may be adjusted, to alter the proportion of particulate material to solvent supplied to the fluidic device(s) 770. In one embodiment, a valve (not shown) may be placed between the reservoir 772 and the tee 778 to control the flow of particulate into the tee 778. The fluidic device(s) 770 are preferably at least partially immersed in a liquid 782 contained by a (ultrasonic) sonicator bath 780. A diluted slurry is supplied to the microfluidic device(s) 770 to permit a slow, dense buildup of particles within the separation channels contained in the device(s) 770.

Yet another column packing system 800 is illustrated in FIG. 11. This fluidized bed design utilizes a vertically disposed vessel 812 containing solvent 816 and particulate

814. Solvent 816 is supplied from a pump 802 via tubing 803 to an inlet 804 disposed at the bottom of the vessel 812. Vertical flow of the solvent 816 supplied by the pump 802 agitates particulate within the vessel 812, thus ensuring that a sufficient amount of particulate 814 becomes entrained in the solvent 816 before exiting the vessel 812 through an outlet 806. One or more baffles (not shown) may be disposed within the vessel 812 above the inlet 804 to improve agitation of the particulate 814. Further factors affecting entrainment include the size of the particulate 814 used, the dimensions of the vessel 812, and the flow rate of the solvent 816 supplied by the pump 802. Slurry is supplied from the vessel 812 to at least one fluidic device 810 through a slurry outlet 806, tubing 807, and a fitting 808 preferably engaged to a clamping apparatus (such as described previously herein) providing a pressure-tight connection to the fluidic device(s) 810. Preferably, valves (not shown) are provided in fluid communication with the tubing 803, 807. The fluidic device 810 is preferably at least partially immersed in a liquid 822 contained by a (ultrasonic) sonicator bath 820. During operation of the system 800, a diluted slurry is supplied to the microfluidic device(s) 810 to permit a slow, dense buildup of particles within the separation channels contained in the device(s) 810.

As compared to conventional methods for packing individual chromatography columns, methods according to the present invention permit much larger number of columns (including both multi-column microfluidic devices and multiple microfluidic devices) to be packed simultaneously. It is believed that the packing methods and apparatuses disclosed herein permit much higher packing throughput and may be scaled to facilitate large production volumes at a modest capital cost. As compared to other methods for packing separation columns, the present methods greatly speed up packing time and are much more scalable to large production volumes.

The particular devices and methods illustrated and described herein are provided by way of example only, and are not intended to limit the scope of the invention. The scope of the invention should be restricted only in accordance with the appended claims and their equivalents.

What is claimed is:

1. A pressure-driven substantially planar liquid chromatography device comprising a plurality of device layers defining a plurality of microfluidic separation channels containing packed stationary phase material.

2. The device of claim 1, further comprising a porous frit in fluid communication with the plurality of microfluidic separation channels, wherein the packed stationary phase material comprises packed particulate material, the particulate material has an average particle size, the frit material has an average pore size, and the average pore size is smaller than the average particle size.

3. The device of claim 2, further comprising a solvent outlet port, a slurry inlet port, and a common junction or manifold region in fluid communication with the plurality of separation channels, wherein stationary phase material is packed within the device according to the following method steps:

supplying a slurry comprising particulate material and a slurry to the slurry inlet port;

applying a pressure differential between the slurry inlet port and the solvent outlet port to promote the flow of slurry into the separation channels; and substantially filling the plurality of separation channels up to the porous frit with slurry.

4. The device of claim 1, further comprising a porous frit disposed between two device layers of the plurality of device layers, the porous frit being in fluid communication with at least one microfluidic separation channel of the plurality of microfluidic separation channels.

5. The device of claim 1 wherein the plurality of microfluidic separation channels are adapted to operate at a pressure greater than or equal to about 10 psi.

6. The device of claim 1 wherein the plurality of microfluidic separation channels are adapted to operate at a pressure greater than or equal to about 100 psi.

7. The device of claim 1 wherein each microfluidic separation channel of the plurality of microfluidic separation channels has a length greater than or equal to about one centimeter.

8. The device of claim 1 wherein at least one layer of the plurality of device layers is a stencil layer.

9. The device of claim 1 wherein the plurality of device layers comprise polymeric materials.

10. The device of claim 1, further comprising:

a stationary phase inlet port; and a splitter disposed between and in fluid communication with the stationary phase inlet port and the plurality of microfluidic separation channels;

wherein the plurality of microfluidic separation channels and the common junction or manifold region are substantially filled with packed stationary phase material.

11. The device of claim 1, further comprising:

a mobile phase inlet port; and a splitter disposed between and in fluid communication with the mobile phase inlet port and the plurality of microfluidic separation channels.

12. The device of claim 1 wherein the packed stationary phase material comprises packed particles, and the particles comprise silicon, zirconium, or polymeric materials.

13. The device of claim 12 wherein the packed particles are unsintered.

14. The device of claim 12 wherein the packed particles comprise at least one surface functional group.

15. The device of claim 14 wherein the at least one surface functional groups is selected from the group consisting of: alkyl, cyano, amino, nitro, hydroxy, phenyl, phenyl-hexyl, and sulfonic acid.

16. The device of claim 1, further comprising a detection region in fluid communication with at least one microfluidic separation column of the plurality of microfluidic separation columns, the detection region permitting detection of at least one property of a substance eluted from the at least one microfluidic separation column.

17. A pressure-driven microfluidic separation device comprising:

a fluidic inlet port;

a fluidic outlet port; and a plurality of microfluidic separation channels in fluid communication with a common junction or manifold region upstream of the outlet port;

wherein the microfluidic separation channels and common junction or manifold region are substantially filled with packed particulate stationary phase material.

18. The device of claim 17 wherein the packed particulate material comprises silicon, zirconium, or polymeric particles.

19. The device of claim 18 wherein the packed particulate material is unsintered.

20. The device of claim 18 wherein the packed particulate material comprises at least one surface functional group.

21. The device of claim 20 wherein the at least one surface functional group is selected from the group consisting of:

alkyl, cyano, amino, nitro, hydroxy, phenyl, phenyl-hexyl, and sulfonic acid.

22. The device of claim 17 wherein the device is constructed with polymeric materials.

23. The microfluidic device of claim 17 wherein the device is constructing with a plurality of device layers including at least one stencil layer having at least one microfluidic channel defined through the entire thickness of the at least one stencil layer.

24. The device of claim 23, further comprising a porous frit disposed between two device layers of the plurality of device layers, the porous frit being in fluid communication with at least one microfluidic separation channel of the plurality of microfluidic separation channels.

25. The microfluidic device of claim 17, further comprising a porous frit disposed between the fluidic outlet port and at least one microfluidic separation channel of the plurality of microfluidic separation channels.

26. The microfluidic device of claim 17, further comprising a porous frit disposed between the fluidic inlet port and at least one microfluidic separation channel of the plurality of microfluidic separation channels.

27. The microfluidic device of claim 17, further comprising a porous frit in fluid communication with the plurality of microfluidic separation channels, wherein the packed stationary phase material comprises packed particulate material, the particulate material has an average particle size, the frit material has an average pore size, and the average pore size is smaller than the average particle size.

28. The microfluidic device of claim 17, further comprising a splitter disposed between the inlet port and the plurality of microfluidic separation channels.

29. The microfluidic device of claim 28 wherein the inlet port and splitter are used to supply mobile phase solvent to each microfluidic separation channel of the plurality of microfluidic separation channels.

30. The microfluidic device of claim 17, further comprising a plurality of fluidic inlet ports.

31. The microfluidic device of claim 17, further comprising a plurality of fluidic outlet ports.

32. The microfluidic device of claim 17, further comprising at least one detection region in fluid communication with at least one microfluidic separation channel of the plurality of separation channels.

33. The device of claim 17 wherein the plurality of microfluidic separation channels are adapted to operate at a pressure greater than or equal to about 10 psi.

34. The device of claim 17 wherein the plurality of microfluidic separation channels are adapted to operate at a pressure greater than or equal to about 100 psi.

35. The device of claim 17 wherein each microfluidic separation channel of the plurality of microfluidic separation channels has a length greater than or equal to about one centimeter.

36. A microfluidic device containing a separation column fabricated according to the following method steps:
providing a device body having a slurry inlet port, an internal void defining a plurality of channels that connect to a common junction or manifold region, and a solvent outlet port downstream of the common junction or manifold region;
supplying a slurry comprising particulate material and a liquid to the slurry inlet port;
applying a pressure differential between the slurry inlet port and the solvent outlet port to promote the flow of slurry into the void; and
substantially filling the common junction or manifold region and the plurality of channels with slurry.

37. A multi-layer pressure-driven liquid chromatography device comprising:
a body structure defining a plurality of microfluidic separation channels;
particulate stationary phase material packed within the plurality of separation channels; and
at least one porous fit adapted to retain the particulate stationary phase material within the plurality of microfluidic separation channels;
wherein the at least one porous frit has an average pore size, the packed particulate stationary phase material has an average particle size, and the average pore size is smaller than the average particle size.

38. The device of claim 37 wherein the body structure comprises a plurality of substantially planar device layers.

39. The device of claim 38 wherein the at least one porous frit comprises a substantially planar porous membrane.

40. The device of claim 39 wherein the at least one porous frit is disposed between two device layers of the plurality of device layers.

41. The device of claim 38 wherein each device layer of the plurality of device layers comprises a polymeric material.

42. The device of claim 38 wherein each device layer of the plurality of device layers and the at least one porous frit comprise polyolefin materials.

43. The device of claim 38 wherein:
each device layer of the plurality of device layers and the at least one porous frit comprise adhesiveless, substantially metal-free polymeric materials;
the at least one porous frit is disposed between two device layers of the plurality of device layers; and
the plurality of device layers are interpenetrably bound to form a substantially sealed microstructure comprising at least a portion of the body structure.

44. The device of claim 38 wherein at least one layer of the plurality of device layers is a stencil layer defining at least one microfluidic channel through the entire thickness of the stencil layer.

45. The device of claim 37 wherein the at least one porous membrane comprises a polymeric material.

46. The device of claim 37 wherein the body structure comprises a polymeric material.

47. The device of claim 37 further comprising at least one fluidic inlet port and a plurality of fluidic outlet ports in fluid communication with the plurality of microfluidic separation channels.

48. The device of claim 37 wherein the at least one porous fit comprises:
at least one first porous frit disposed between the at least one fluidic inlet port and the plurality of microfluidic separation channels; and
at least one second porous frit disposed between the plurality of fluidic outlet ports and the plurality of microfluidic separation channels.

49. The device of claim 48 wherein the at least one fluidic inlet port comprises a plurality of fluidic inlet ports.

50. The device of claim 37 wherein the at least one porous frit comprises a first unitary frit spanning across at least a portion of each separation column of the plurality of separation columns.

51. The device of claim 37, further comprising:
a stationary phase inlet port; and
a common junction or manifold region disposed between, and in fluid communication with, the stationary phase inlet port and the plurality of microfluidic separation channels;

wherein the plurality of microfluidic separation channels and the common junction or manifold region are substantially filled with packed particulate stationary phase material.

52. The device of claim 37 further comprising:

a mobile phase inlet port; and a fluidic distribution network disposed between, and in fluid communication with, the mobile phase inlet port and the plurality of microfluidic separation channels.

53. The device of claim 37 wherein the packed particulate stationary phase material includes particles comprising any of silicon, zirconium, and polymeric materials.

54. The device of claim 37 wherein the packed particulate stationary phase material is unsintered.

55. The device of claim 37 wherein the packed particulate stationary phase material comprises at least one surface functional group.

56. The device of claim 55 wherein the at least one surface functional group comprises any of alkyl, cyano, amino, nitro, hydroxy, phenyl, phenyl-hexyl, and sulfonic acid.

57. The device of claim 37, further comprising a detection region in fluid communication with at least one microfluidic separation channel of the plurality of microfluidic separation channels.

* * * * *

UNITED STATES PATENT AND TRADEMARK OFFICE
CERTIFICATE OF CORRECTION

PATENT NO. : 6,923,907 B2 Page 1 of 1
APPLICATION NO. : 10/366985
DATED : August 2, 2005
INVENTOR(S) : Hobbs, Steven E. et al.

It is certified that error appears in the above-identified patent and that said Letters Patent is hereby corrected as shown below:

In Column 11, Line 3, "611-617" should be -- 611-618 --.

Signed and Sealed this

Eighth Day of August, 2006

JON W. DUDAS
*Director of the United States Patent and Trademark Office*